US006537579B1

(12) United States Patent
Desai et al.

(10) Patent No.: US 6,537,579 B1
(45) Date of Patent: Mar. 25, 2003

(54) COMPOSITIONS AND METHODS FOR ADMINISTRATION OF PHARMACOLOGICALLY ACTIVE COMPOUNDS

(75) Inventors: Neil P. Desai, Los Angeles, CA (US); Patrick Soon-Shiong, Los Angeles, CA (US)

(73) Assignee: American BioScience, Inc., Santa Monica, CA (US)

(*) Notice: Subject to any disclaimer, the term of this patent is extended or adjusted under 35 U.S.C. 154(b) by 0 days.

(21) Appl. No.: 09/574,763

(22) Filed: May 19, 2000

Related U.S. Application Data

(63) Continuation-in-part of application No. 09/446,783, filed as application No. PCT/US98/13272 on Jun. 26, 1998, and a continuation-in-part of application No. 09/316,642, filed on May 21, 1999, which is a continuation-in-part of application No. 09/198,082, filed on Nov. 23, 1998, now abandoned, which is a division of application No. 08/720,756, filed on Oct. 1, 1996, now Pat. No. 5,916,596, which is a continuation-in-part of application No. 08/412,726, filed on Mar. 29, 1995, now Pat. No. 5,560,933, which is a continuation-in-part of application No. 08/023,698, filed on Feb. 22, 1993, now Pat. No. 5,439,686, application No. 09/574,763, which is a continuation-in-part of application No. 08/926,155, filed on Sep. 7, 1997, now Pat. No. 6,096,331, which is a continuation-in-part of application No. 08/200,235, filed on Feb. 24, 1994, now Pat. No. 5,498,421.

(60) Provisional application No. 60/051,021, filed on Jun. 27, 1997.

(51) Int. Cl.[7] .................................................. A61K 9/14

(52) U.S. Cl. ..................................................... 424/489

(58) Field of Search ......................................... 424/489

(56) References Cited

U.S. PATENT DOCUMENTS

| 4,073,943 A | 2/1978 | Wretlind et al. ............. 424/358 |
| 4,344,934 A | 8/1982 | Martin et al. ................... 424/80 |
| 4,671,954 A | 6/1987 | Goldberg et al. ............ 424/450 |
| 5,041,292 A | 8/1991 | Feijen ......................... 424/484 |
| 5,059,699 A | 10/1991 | Kingston et al. ............ 549/511 |
| 5,145,684 A | 9/1992 | Liversidge et al. .......... 424/489 |
| 5,270,052 A | * 12/1993 | Gelfand et al. .............. 424/450 |
| 5,362,478 A | 11/1994 | Desai et al. .................... 424/9 |
| 5,399,363 A | 3/1995 | Liversidge et al. .......... 424/490 |
| 5,439,686 A | 8/1995 | Desai et al. ................. 424/451 |
| 5,498,421 A | 3/1996 | Grinstaff et al. ............. 424/450 |
| 5,504,102 A | 4/1996 | Agharkar et al. ............ 514/449 |
| 5,505,932 A | 4/1996 | Gristaff et al. ................ 424/9.3 |
| 5,508,021 A | 4/1996 | Grinstaff et al. ......... 424/9.322 |
| 5,512,268 A | 4/1996 | Grinstaff et al. ......... 424/9.322 |
| 5,543,152 A | 8/1996 | Webb et al. .................. 424/450 |
| 5,560,933 A | 10/1996 | Soon-Shing et al. ........ 424/489 |
| 5,565,478 A | 10/1996 | Kohn et al. .................. 514/359 |
| 5,626,862 A | 5/1997 | Brem et al. .................. 424/426 |
| 5,631,018 A | 5/1997 | Zalipsky et al. ............. 424/450 |
| 5,648,090 A | 7/1997 | Rahman et al. .............. 424/450 |
| 5,683,715 A | 11/1997 | Boni et al. ................... 424/450 |
| 5,714,166 A | 2/1998 | Tomalia et al. .............. 424/486 |
| 5,723,147 A | 3/1998 | Kim et al. .................... 424/450 |
| 5,731,334 A | 3/1998 | Wrasidlo ...................... 514/358 |
| 5,744,460 A | 4/1998 | Müller et al. ................... 514/44 |
| 5,766,627 A | 6/1998 | Sankaram et al. ........... 424/450 |
| 5,916,596 A | 6/1999 | Desai et al. .................. 424/489 |
| 5,977,163 A | 11/1999 | Li et al. ....................... 514/449 |
| 6,096,331 A | 8/2000 | Desai et al. .................. 424/422 |

FOREIGN PATENT DOCUMENTS

| EP | 0 123 456 A2 | 10/1984 | |
| FR | 2 660 556 | 4/1990 | ............ A61K/9/51 |
| WO | WO 85/00011 | 1/1985 | ............ A61K/9/22 |
| WO | WO 94/10980 | 5/1994 | ............ A61K/9/14 |

OTHER PUBLICATIONS

Liversidge–Merisko et al., "Formulation and Antitumor Activity Evaluation of Nanocrystalline Suspensions of Poorly Soluble Anticacer Drugs" *Pharmaceutical Research*, 13(2):272–278 (1996).

Norton et al., *Abstracts of the 2nd National Cancer Institute Workshop on Taxol & Taxus*, Sep. 23–24, 1992).

Wani et al., "Plant Antitumor Agents. VI. The Isolation and Structure of Toxol, a Novel Antileukemic and Antitumor Agents from *Taxus brevifolia*[1,2]" *J. Am. Chem. Soc.*, 93:2325–2327 (1971).

Gref, Ruxandra, et al., "Biodegradable Long–Circulating Polymeric Nanospheres," *Science* 263:1600–1603 (1994).

(List continued on next page.)

*Primary Examiner*—Alton Pryor
(74) *Attorney, Agent, or Firm*—Stephen E. Reiter; Foley & Lardner

(57) ABSTRACT

In accordance with the present invention, there are provided compositions and methods useful for the in vivo delivery of substantially water insoluble pharmacologically active agents (such as the anticancer drug paclitaxel) in which the pharmacologically active agent is delivered in the form of suspended particles coated with protein (which acts as a stabilizing agent). In particular, protein and pharmacologically active agent in a biocompatible dispersing medium are subjected to high shear, in the absence of any conventional surfactants, and also in the absence of any polymeric core material for the particles. The procedure yields particles with a diameter of less than about 1 micron. The use of specific composition and preparation conditions (e.g., addition of a polar solvent to the organic phase), and careful election of the proper organic phase and phase fraction, enables the reproducible production of unusually small nanoparticles of less than 200 nm diameter, which can be sterile-filtered. The particulate system produced according to the invention can be converted into a redispersible dry powder comprising nanoparticles of water-insoluble drug coated with a protein, and free protein to which molecules of the pharmacological agent are bound. This results in a unique delivery system, in which part of the pharmacologically active agent is readily bioavailable (in the form of molecules bound to the protein), and part of the agent is present within.

53 Claims, No Drawings

OTHER PUBLICATIONS

Gabizon, Alberto A.,. "Selective Tumor Localization and Improved Therapeutic Index of Anthracyclines Encapsulated in Long–Circulating Liposomes," *Cancer Research* 52:891–896 (1992).

Nicolaou, K.C., et al., "Chemical Biology of Epothilones," *Angew. Chem. Int. Ed.* 37:2014–2045 (1998).

Dvorak, Harold F., et al., "Identification and Characterization of the Blood Vessels of Solid Tumors That Are Leaky to Circulating Macromolecules," *Amer. J. Path.* 133(1):95–109 (1988).

Holmes, Frankie Ann, et al., Phase II Trial of Taxol, an Active Drug in the Treatment of Metastatic Breast Cancer, *J. Nat'l Canc. Inst.* 83(24):1797–1805 (1991).

Papahadjopoulos, D., et al., "Sterically Stabilized Liposome: Improvements in Pharmacokinetics and Antitumor Therapeutic Efficacy," *Proc. Natl. Acad. Sci* 88:11460–11464 (1991).

Lorenz, W., et al., "Histamine Release in Dogs by Cremohor EI® and its Derivatives: Oxethylated Oleic Acid is the Most Effective Constituent" *Agents and Actions* 7(1):63–67 (1977).

Reichman, Bonnie S., et al., "Paclitaxel and Recombinant Human Granulocyte Colony–Stimulating Factor as Initial Chemotherapy for Metastatic Breast Cancer," *J. Clin. Oncology* 11(10):1943–1951 (1993).

Weiss, Raymond B., et al., "Hypersensitivity Reactions From Taxol," *J. Clin. Oncol.* 8(7):1263–1268 (1990).

Dunn, Susan E., et al., "Polystyrene–Poly (Ethylene Glycol) (PS–PEG2000) Particles as Model Systems for Site Specific Drug Delivery," *Pharm. Res.* 11(7):1016–1022 (1994).

Physicians' Desk Reference (52 Ed. 1998).

Drug Facts and Comparisons (1999 Ed., pp. 3548–1558).

Onoe, Yoshiko, et al., IL–13 and IL–4 Inhibit Bone Resorption by Suppressing Cyclooxygenase–2–Dependent Prostaglandin Synthesis in Osteoblasts, *J. of Immunologyl* 758–764 (1996).

Mitchell, Jane A., et al., "Selectivity of Nonsteroidal Anti-inflammatory Drugs as Inhibitors of Constitutive and Inducible Cyclooxygenase," *Proc. Natl. Acad. Sci. USA* 90:11693–11697 (1994).

Glaser, Keith, et al., "Etodolac Selectively Inhibits Human Prostaglandin G/H Synthase 2 (PGHS–2) Versus Human PGHS–1," *European J. of Pharm.* 281:107–111 (1995).

Carson, Jeffrey L., et al., "The Relative Gastrointestinal Toxicity of the Nonsteroidal Anti–Inflammatory Drugs," *Arch Intern. Med.* 147:1054–1059 (1987).

Slater, Donna M., et al., "Expression of Cyclooxygenase Types 1 and 2 in Human Fetal Membranes at Term," *Am. J. Obstet. Gynecol.* 172, No. 1, Pt. 1:77–82 (1995).

Graham, David Y., et al., "Nonsteroidal Anti–Inflammatory Effect of Sulindac Sulfoxide and Sulfide on Gastric Mucosa," *Clin. Pharmacol. Ther.*, 65–70 (1985).

Bjarnason, Ingvar, et al., "Side Effects of Nonsteroidal Anti–Inflammatory Drugs on the Small and Large Intestine in Humans," *Gastroenterology* 104:1832–1847 (1993).

Kargman, Stacia, "Characterization of Prostaglandin G/H Synthase 1 and 2 in Rat, Dog, Monkey, and Human Gastrointestinal Tracts," *Gastroenterology* 111:445–454 (1996).

Wallace, John L., "Nonsteroidal Anti–Inflammatory Drugs and Gastroenteropathy: The Second Hundred Years," *Gastroenterology* 112:1000–1016 (1997).

Kaplan–Machlis, Barbara et al., "The Cyclooxygenase–2 Inhibitors: Safety and Effectiveness," *The Annals of* Pharmacotherapy 33:979–988 (1999).

Soll, Andrew H., "Nonsteroidal Anti–Inflammatory Drugs and Peptic Ulcer Disease," *Annals of Intern. Med.* 114 (4):307–319 (1991).

Meade, Elizabeth, et al., "Differential Inhibition of Prostaglandin Endoperoxide Synthase (Cyclooxygenase) Isozymes by Aspirin and Other Non–Steroidal Anti–Inflammatory Drugs," *J.Biol.Chem.* 268(9):6610–6614 (1993).

Bazile, et al., "Body Distribution of Fully Biodegradable [$^{14}$C]–Poly(Lactic Acid) Nanoparticles Coated With Albumin After Parenteral Administration to Rats," *Biomaterials*, 13/15:1093–1102, (1992).

Bodmeier et al., "Solvent Selection in the Preparation of Poly(DL–Lactide) Microspheres Prepared by the Solvent Evaporation Method," *International Journal of Pharmaceutics*, 43:79–186, (1988).

Boury et al., "Dilatational Properties of Adsorbed Poly(D, L–Lactide) and Bovine Serum Albumin Monolayers at the Dichloromethane/Water Interface," *Langmuir*, 11:1636–1644, (1995).

Calvo, et al. "Comparative In Vitro Evaluation of Several Colloidal Systems, Nanoparticles, Nanocapsules, and Nanoemulsions, as Ocular Drug Carriers," *Journal of Pharmaceutical Sciences*, 85/5:530–536, (1996).

Cavalier et al., "The Formation and Characterization of Hydrocortisone Loaded Poly((+,–)–Lactide Microspheres," *J. Pharm. Pharmacol*, 38:249–253, (1986).

Fletcher et al., "Antinociceptive Effect of Bupivacaine Encapsulated in Poly(D,L)–Lactide–Co–Glycolide Microspheres in the Acute Inflammatory Pain Model of Carrageenin–Injected Rats," *Anesth. Analg.*, 84:90–94, (1997).

Kumar et al., "Binding of Taxol to Human Plasma, Albumin, and $\alpha_1$–Acid Glycoprotein," *Research Communications in Chemical Pathology and Pharmacology*, 80/3:337–344, (1993).

Lee et al., "Serum Albumin Beads: An Injectable, Biodegradable System for the Sustained Release of Drugs," *Science*, 213:233–235, (1981).

Leucata et al., "Albumin Microspheres as a Drug Delivery System for Epirubicin: Pharmaceutical, Pharmacokinetic and Biological Aspects," *International Journal of Pharmaceutics*, 41:213–217, (1988).

Mathew et al., "Synthesis and Evaluation of Some Water–Soluble Prodrugs and Derivatives of Taxol with Antitumor Activity," *J. Med. Chem.*, 35:145–151, (1992).

Sjostrom et al., "The Formation of Submicron Organic Particles by Precipitation in an Emulsion," *Journal of Dispersion Science and Technology*,15/1:89–117, (1994).

Tice et al., "Preparation of Injectable Controlled–Release Microcapsules by a Solvent–Evaporation Process," *Journal of Controlled Release*, 2:343–352, (1985).

\* cited by examiner

COMPOSITIONS AND METHODS FOR ADMINISTRATION OF PHARMACOLOGICALLY ACTIVE COMPOUNDS

RELATED APPLICATIONS

This application is a continuation-in-part of U.S. Ser. No. 09/446,783, filed Dec. 27, 1999, now pending, which claims priority from PCT Application No. PCT/US98/13272, filed Jun. 26, 1998, now completed, which claims priority from U.S. Ser. No. 60/051,021, filed Jun. 27, 1997, now abandoned; as well as a continuation-in-part of U.S. Ser. No. 09/316,642, filed May 21, 1999, now pending, which is a continuation-in-part of U.S. Ser. No. 09/198,082, filed Nov. 23, 1998, now abandoned, which is a divisional of U.S. Ser. No. 08/720,756, filed Oct. 1, 1996, now issued as U.S. Pat. No. 5,916,596, which is a continuation-in-part of U.S. Ser. No. 08/412,726, filed Mar. 29, 1995, now issued as U.S. Pat. No. 5,560,933, which is a continuation-in-part of U.S. Ser. No. 08/023,698, filed Feb. 22, 1993, now issued as U.S. Pat. No. 5,439,686; as well as a continuation-in-part of U.S. Ser. No. 08/926,155, filed Sep. 7, 1997, now U.S. Pat. No. 6,096,331 which is a continuation-in-part of U.S. Ser. No. 08/200,235, filed Feb. 24, 1994, now issued as U.S. Pat. No. 5,498,421, the contents of each of which are hereby incorporated by reference herein in their entirety.

FIELD OF THE INVENTION

The present invention relates to methods for the production of particulate vehicles for the intravenous administration of pharmacologically active agents, novel compositions produced thereby, and methods for in vivo delivery thereof.

BACKGROUND OF THE INVENTION

The anticancer agent paclitaxel (TAXOL for Injection Concentrate, Bristol Myers Squibb (BMS)) has remarkable clinical activity in a number of human cancers including cancers of the ovary, breast, lung, esophagus, head and neck region, bladder and lymphomas. It is currently approved for the treatment of ovarian carcinoma and non-small cell lung cancer where it is used in combination with cisplatin; for metastatic breast cancer that has failed prior treatment with one combination chemotherapy regimen; and for AIDS-related Kaposi's sarcoma. The major limitation to the use of paclitaxel is its poor solubility and consequently the BMS formulation (TAXOL) contains Cremophor® EL as the solubilizing vehicle. Each vial of TAXOL contains 30 mg of paclitaxel dissolved in Cremophor/ethanol vehicle at a concentration of 6 mg/mL. Prior to intravenous administration, this formulation must be diluted 1:10 in saline to produce a final dosing solution containing 0.6 mg/mL of paclitaxel. The presence of Cremophor in this formulation has been linked to severe hypersensitivity reactions in animals (Lorenz et al., 1987, "Histamine Release in Dogs by Cremphor EL® and its derivatives: Oxethylated oleic acid is the most effective constituent". Agents Actions 7:63–67, 1987) and humans (Weiss et al., 1990, "Hypersensitivity reactions from Taxol", J Clin Oncol 8:1263–1268, 1990) and consequently requires premedication of patients with corticosteroids (dexamethasone) and antihistamines. The large dilution results in large volumes of infusion (typical dose 175 mg/m$^2$) in up to one liter and infusion times ranging from three hours to 24 hours. Thus, there is a need for an alternative, less toxic formulation for paclitaxel.

In a study by Holmes (Holmes F A, Walters R S, Theriault R L, et al: Phase II trial of Taxol, an active drug in the treatment of metastatic breast cancer. J Natl Cancer Inst 83:1797–1805, 1991) and at MKSCC (Reichman B S, Seidman A D, Crown J P A, et al: Paclitaxel and recombinant human granulocyte colony stimulating factor as initial chemotherapy for metastatic breast cancer. Clin Oncol 11:1943–1951, 1993) it was shown that higher doses of TAXOL to 250 mg/m$^2$ produced greater responses (60%) than the 175 mg/m$^2$ dose (26%) currently approved for TAXOL. These results however, have not been reproduced due to higher toxicities at these higher doses. These studies, however, bear proof to the potential increase in response rate at increased doses of paclitaxel. The invention formulations described herein may allow the administration of highter doses then are possible with TAXOL due to lower toxicity of the formulation, thereby exploiting the full potential of this drug.

Bristol-Myers Squibb tested TAXOL in clinical trials on patients previously treated for ovarian and breast cancer that did not respond to standard therapies. Following are summaries of information as reported in the package insert for TAXOL:

Following intravenous administration of TAXOL, paclitaxel plasma concentrations declined in a biphasic manner. The initial rapid decline represents distribution to the peripheral compartment and elimination of the drug. The later phase is due, in part, to a relatively slow efflux of paclitaxel from the peripheral compartment.

With the 24-hour infusion of TAXOL, it appeared that an increase in dose from 135 mg/m$^2$ to 175 mg/m$^2$ (30%) increased the $C_{max}$ by 87% whereas the AUC (0–∞) remained proportional. However, with a 3-hour infusion, the dose increase from 135 to 175 mg/m$^2$ caused an increase in the $C_{max}$ and AUC (0–∞) of 68% and 89%, respectively. The mean apparent volume of distribution with the 24-hour infusion of TAXOL ranged from 227 to 688 L/m$^2$, indicating extensive extravascular distribution and/or tissue binding of paclitaxel.

In Phase I and II studies, pharmacokinetics of TAXOL were also evaluated in adult cancer patients who received single doses of 15–135 mg/m$^2$ given by 1-hour infusions (n=15), 30–275 mg/m$^2$ given by 6-hour infusions (n=36), and 200–275 mg/m$^2$ given by 24-hour infusions (n=54). Values from these studies were consistent with the findings in the above study.

In vitro studies were used to study the binding of paclitaxel to human serum proteins. Between 89–98% of drug was bound for paclitaxel concentrations ranging from 0.1 to 50 μg/mL. The presence of cimetidine, ranitidine, dexamethasone, or diphenhydramine did not affect protein binding of paclitaxel.

The disposition of paclitaxel has not been fully elucidated in humans. Mean (SD) values for cumulative urinary recovery of unchanged drug ranged from 1.3% (0.5%) to 12.6% (16.2%) of the dose after intravenous administration, indicating extensive non-renal clearance for 15–275 mg/m$^2$ doses of TAXOL as 1, 6, or 24-hour infusion. Since TAXOL has been demonstrated to be metabolized in the liver in animals, the evidence suggests hepatic metabolism in humans. In addition, high paclitaxel concentrations have been reported in the bile of patients treated with TAXOL. However, effects of renal or hepatic dysfunction on the disposition of paclitaxel have not been investigated.

Review of recent literature indicates that there are several Phase I and II studies in progress to study possible interactions of paclitaxel with concomitantly administered medications. In general, platinum-based concomitant therapies and sequence/time intervals influence both toxicity and efficacy. Also, paclitaxel can function as a radiosensitizer when used in combination with radiation therapy.

The initial approval of the TAXOL formulation of paclitaxel was based on Phase I and II studies of 189 patients and a Phase III study with 407 patients who had failed initial or subsequent chemotherapy for metastatic carcinoma of the ovary. In the first 2 studies, response rates were 22% (95% Cl=11–37%) and 30% (95% Cl=18–46%) with a total of six complete and 18 partial responses in 92 patients.

The median duration of overall response in these two studies measured from the first day of treatment was 7.2 months (range: 3.5–15.8 months) and 7.5 months (range: 5.3–17.4 months), respectively. The median survival was 8.1 months (range: 0.2–36.7 months) and 15.9 months (range: 1.8–34.5 months).

The Phase III study compared the efficacy and safety of TAXOL, administered at 135 or 175 mg/m$^2$ paclitaxel with either three or 24 hour infusion schedules. The results are summarized in Table 1.

TABLE 1

Key Efficacy Parameters in the Phase III Ovarian Carcinoma Study

| Parameter | TAXOL dose (mg/m$^2$/hrs) | | | |
|---|---|---|---|---|
| | 175/3 (N = 96) | 175/24 (N = 106) | 135/3 (N = 99) | 135/24 (N = 106) |
| Response rate (percent) | 14.6 | 21.7 | 15.2 | 13.2 |
| Time to progression median (months) | 4.4 | 4.2 | 3.4 | 2.8 |
| Survival median (months) | 11.5 | 11.8 | 13.1 | 10.7 |

The most frequently observed adverse events involved myelosuppression with 352 episodes of neutropenia of <2,000/mm$^3$ and 183 episodes of neutropenia of <500/mm$^3$. Episodes of thrombocytopenia with <100,000/m$^3$ and <50,000/m$^3$ were 36 and 11, respectively. Episodes of anemia with <11 g/dL and <8 g/dL were 330 and 39, respectively. There were also 93 episodes of infection. There were 169 episodes of hypersensitivity reactions, five of which were severe. Also there were 220 observations of peripheral neuropathy (with three severe cases) and 98 observations of mucositis (with three severe cases).

The initial approval of the TAXOL formulation of paclitaxel for use on patients with breast cancer after failure of combination chemotherapy for metastatic disease or relapse within six months of adjuvant chemotherapy was based on data from 83 patients in three Phase II studies. TAXOL was administered to 53 patients as a 24-hour infusion at initial doses of 250 mg/m$^2$ (with G-CSF support) or 200 mg/m$^2$ in two Phase II studies. The response rates were 57% (95% CI: 37–75%) and 52% (95% CI: 32–72%), respectively. A third Phase II study was conducted in extensively pretreated patients who had failed anthracycline therapy and who had received a minimum of two chemotherapy regimens for the treatment of metastatic disease. The dose of TAXOL was 200 mg/m$^2$ paclitaxel as a 24-hour infusion with G-CSF support. Nine of the 30 patients analyzed achieved a partial response, for a response rate of 30% (95% CI: 15–50%).

A multicenter, Phase III trial with 471 patients was conducted in patients previously treated with one or two regimens of chemotherapy. Patients received TAXOL at a dose of either 175 mg/m$^2$ or 135 mg/m$^2$ paclitaxel given as a 3-hour infusion. Sixty percent of the patients had symptomatic disease with impaired performance status at study entry, and 73% had visceral metastases. All patients had failed prior chemotherapy, 67% had been previously exposed to anthracyclines and 23% of them had disease considered resistant to this class of agents. The overall response rate for the 454 evaluable patients was 26% with 17 complete and 99 partial responses. The median duration of response was 8.1 months (range: 3.4–18.1 months) and median survival was 11.7 months (range: 0–18.9 months). Adverse events observed were similar to the type and frequency recorded for ovarian cancer patients treated with paclitaxel. Table 2 shows the incidence of some key adverse events for the Phase III study.

TABLE 2

Frequency of Key Adverse Events in the Phase III Breast Carcinoma Study

| | | Percent of Patients | |
|---|---|---|---|
| Adverse Event | | 175 mg/m$^2$ (N = 229) | 135 mg/m$^2$ (N = 229) |
| Bone Marrow | | | |
| Neutropenia | <2,000/mm$^3$ | 90 | 81 |
| | <500/mm$^3$ | 28 | 19 |
| Thrombocytopenia | <100,000/mm$^3$ | 11 | 7 |
| | <50,000/mm$^3$ | 3 | 2 |
| Anemia* | <11 g/dL | 55 | 47 |
| | <8 g/dL | 4 | 2 |
| Infections | | 23 | 15 |
| Febrile Neutropenia | | 2 | 2 |
| Hypersensitivity Reaction** | | | |
| All | | 36 | 31 |
| Severe | | 0 | <1 |
| Peripheral Neuropathy | | | |
| Any symptoms | | 70 | 46 |
| Severe symptoms | | 7 | 3 |
| Mucositis | | | |
| Any symptoms | | 23 | 17 |
| Severe symptoms | ≧ Grade 3 | 3 | <1 |

*Based on worst course analysis
**All patients received premedication

Myelosuppression and peripheral neuropathy were dose-related. There was one severe hypersensitivity reaction (HSR) observed at the dose of 135 mg/m$^2$.

For the treatment of Non-Small Cell Lung Carcinoma (NSCLC) with TAXOL, 559 patients were randomized to receive either a) TAXOL (T) 135 mg/m$^2$ as a 24-hour infusion in combination with Cisplatin 75 mg/m$^2$, b) TAXOL (T) 250 mg/m$^2$ as a 24 hour infusion in combination with Cisplatin 75 mg/m$^2$ with G-CSF support, or c) Cisplatin 75 mg/m$^2$ on day 1, followed by Etoposide 100 mg/m$^2$ on days 1, 2 and 3 (control).

The adverse event profile was consistent with the profile seen in other clinical studies of TAXOL. Response rates were 25% (TAXOL 135 mg/m$^2$, 24 hour infusion, Cisplatin 75 mg/m$^2$); 23% (TAXOL 25 mg/m$^2$, 24 hour infusion, Cisplatin 75 mg/m$^2$), and 12% (Etoposide 100 mg/m$^2$ and Cisplatin 100 mg/m$^2$).

The approval of the TAXOL formulation of paclitaxel for use as a second line defense on patients with AIDS-related Kaposi's Sarcoma was based on 2 Phase II clinical studies. Paclitaxel doses of 45 mg/m$^2$/week and 50 mg/m$^2$/week were tested. The median time to response was 8.1 weeks and duration of response was 11.0 weeks. Of the 59 patients treated, 3% (2) had complete responses, 56% (33) partial responses, 29% (17) had stable disease, 8% (5) had disease progression and 3% (2) had early death/toxicity. The adverse reactions were similar to patients after treatment for solid tumors. However, patients with AIDS-related Kaposi's Sarcoma may experience more severe hematologic toxicities.

Thus, there remains a need in the art for alternative methods of delivering pharmacologically active agents, such as paclitaxel.

BRIEF DESCRIPTION OF THE INVENTION

In accordance with the present invention, we have discovered that substantially water insoluble pharmacologically active agents can be delivered in the form of microparticles or nanoparticles that are suitable for parenteral administration in aqueous suspension. This mode of delivery obviates the necessity for administration of substantially water insoluble pharmacologically active agents (e.g., paclitaxel) in an emulsion containing, for example, ethanol and polyethoxylated castor oil, diluted in normal saline (see, for example, Norton et al., in Abstracts of the 2nd National Cancer Institute Workshop on Taxol & Taxus, Sep. 23–24, 1992). A disadvantage of such known compositions is their propensity to produce allergic side effects.

Thus, in accordance with the present invention, there are provided methods for the formation of nanoparticles of pharmacologically active agents by a solvent evaporation technique from an oil-in-water emulsion prepared under conditions of high shear forces (e.g., sonication, high pressure homogenization, or the like), optionally without the use of any conventional surfactants and/or without the use of any polymeric core material to form the matrix of the nanoparticle. Instead, proteins (e.g., human serum albumin) are employed as a stabilizing agent.

The invention further provides methods for the reproducible formation of unusually small nanoparticles (less than 200 nm diameter), which can be sterile-filtered through a 0.22 micron filter. This is achieved by addition of a water soluble solvent (e.g., ethanol) to the organic phase and by carefully selecting the type of organic phase, the phase fraction and the drug concentration in the organic phase. The ability to form nanoparticles of a size that is filterable by 0.22 micron filters is of great importance and significance, since formulations which contain a significant amount of any protein (e.g., albumin), cannot be sterilized by conventional methods such as autoclaving, due to the heat coagulation of the protein.

In accordance with another embodiment of the present invention, we have developed compositions useful for in vivo delivery of substantially water insoluble pharmacologically active agents. Invention compositions comprise substantially water insoluble pharmacologically active agents (as a solid or liquid) coated by an optionally crosslinkable biocompatible polymer, and optionally contained within a polymeric shell. The polymeric shell is a crosslinked biocompatible polymer. The polymeric shell, containing substantially water insoluble pharmacologically active agents therein, can then be suspended in a biocompatible aqueous liquid for administration.

The invention further provides a drug delivery system in which part of the molecules of pharmacologically active agent are bound to the protein (e.g., human serum albumin), and are therefore immediately bioavailable upon administration to a mammal. The other portion of the pharmacologically active agent is contained within nanoparticles coated by protein. The nanoparticles containing the pharmacologically active agent are present as a substantially pure active component, without dilution by much, if any, polymeric matrix.

In accordance with the present invention, there are also provided submicron particles in powder form, which can easily be reconstituted in water or saline. The powder is obtained after removal of water by lyophilization. Human serum albumin serves as the structural component of invention nanoparticles, and also as a cryoprotectant and reconstitution aid. The preparation of particles filterable through a 0.22 micron filter according to the invention method as described herein, followed by drying or lyophilization, produces a sterile solid formulation useful for intravenous injection.

The invention provides, in a particular aspect, a composition of anti-cancer drugs, e.g., paclitaxel, in the form of nanoparticles in a liquid dispersion or as a solid which can be easily reconstituted for administration. Due to specific properties of certain drugs, e.g., paclitaxel, such compositions cannot be obtained by conventional solvent evaporation methods that rely on the use of surfactants. In the presence of various surfactants, very large drug crystals (e.g., size of about 5 microns to several hundred microns) are formed within a few minutes of storage, after the preparation process. The size of such crystals is typically much greater than the allowed size for intravenous injection.

While it is recognized that particles produced according to the invention can be either crystalline, amorphous, or a mixture thereof, it is generally preferred that the drug be present in the formulation in an amorphous form. This would lead to greater ease of dissolution and absorption, resulting in better bioavailability.

In accordance with another embodiment of the present invention, there are provided various methods of administering a pharmacologically active agent which must be administered in multiple doses over a cycle time which is less than the cycle time of administration of non-invention formulations of the pharmacologically active agent.

The invention further provides various methods of reducing the myelosuppressive effects and/or the neurotoxic effects of a pharmacologically active agent administered to a patient in need thereof.

In accordance with yet another embodiment of the present invention, there are provided methods of administering pharmacologically active agent(s) to a patient having a disease capable of treatment by the pharmacologically active agent(s). Invention methods comprise administering formulations according to the invention containing suitable pharmacologically active agent(s) to the patient. Diseases contemplated for treatment according to the invention include cancers, proliferative diseases, and the like. Administration of invention formulations can be accomplished in a variety of ways, e.g., intravenous or intraarterial, and/or can be without the use of steroids and/or cytokines, and/or can be in combination with a biochemotherapy agent; and/or the single dose levels of pharmacologically active agents can be greater than about 50 mg; and/or the cumulative dose levels of pharmacologically active agents can be greater than about 250 mg/m$^2$ every 3 weeks.

In accordance with a further embodiment of the present invention, there are provided methods of delivering a pharmacologically active agent to a localized area of a patient for sustained release of the pharmacologically active agent over an extended period of time (e.g., from about 1 day to about 1 year). Invention methods comprise administering to the patient a suitable pharmacologically active agent in the invention formulation, wherein the invention formulation has been dispersed within a matrix of suitable biocompatible material.

In accordance with yet another embodiment of the present invention, there are provided methods of orally administering pharmacologically active agent(s) to a patient in need thereof. Invention methods comprise orally administering an invention formulation of the pharmacologically active agent(s) in combination with intestinal cell efflux inhibitor(s).

In accordance with still another embodiment of the present invention, there are provided methods of administering a combination of suitable pharmacologically active agent(s) to a patient in need thereof. Invention methods comprise administering to the patient 25–75% of the conventionally effective dosage level of each of the suitable pharmacologically active agent(s) in the invention formulation.

DETAILED DESCRIPTION OF THE INVENTION

In accordance with the present invention, there are provided methods for the preparation of substantially water insoluble pharmacologically active agents for in vivo delivery. Also provided in accordance with the invention are compositions prepared by the invention method.

ABI-007 is a proprietary new, Cremophor-free, protein stabilized, nanoparticle formulation of the anticancer drug paclitaxel. Based on animal studies and a Phase I open-label, dose-ranging study, it is believed that a Cremophor-free formulation will be significantly less toxic and will not require premedication of patients. Premedication is necessary with TAXOL to reduce the hypersensitivity and anaphylaxis that occurs as a result of Cremophor in the currently approved and marketed Bristol Myers Squibb formulation of paclitaxel.

In contrast to TAXOL, invention formulations of paclitaxel are stabilized with Human Albumin, USP as vehicle. This combination creates a colloid when reconstituted with saline, which is administered by intravenous infusion. By excluding toxic emulsifiers from invention formulations, it may be possible to administer higher doses of paclitaxel at more frequent intervals than is currently possible with TAXOL.

This unique protein formulation of paclitaxel reduces the toxicities associated with TAXOL (and the Cremophor solvent) while maintaining or improving the chemotherapeutic effect of the drug. The potential exists that enhanced efficacy could be seen in solid tumors as a consequence of (i) higher tolerable doses (300 mg/m$^2$), (ii) longer half-life, (iii) prolonged local tumor availability and/or (iv) sustained in vivo release.

It is known that colloidal nanoparticles or particles <200 nm in size tend to concentrate at the tumor site due to leaky vasculatures. This effect has been described for several lipsomal formulations (Papahadjopoulos, et al., 1991; "Sterically Stabilized Liposomes: improvements in pharmacokinetics, and anti-tumor therapeutic efficacy", Proc. Natl. Acad. Sci. U.S.A. 88,11460,1991; Gabizon, A., 1992, "Selective tumor localization and improved therapeutic index of anthracyclines encapsulated in long-circulating liposomes", Cancer Res., 52,891,1992; Dvorak, et al., 1988, "Identification and Characterization of the blood vesels of solid tumors that are leaky to circulating macromolecules", Am. J. Pathol., 133,95,1988; Dunn, et al., 1994, Polystyrene-pol(ethylene glycol) PS-PEG 2000 particles as model systems for site specific drug delivery: The effect of PEG surface density on the in vitro cell interactions and in vivo biodistribution. Pharm, Res., 11:1016–1022 (1994); and Gref, et al, 1994); Biodegradable long-circulating polymeric nanospheres. Science 263:1600–1603 (1994)). It is possible that localized nanoparticles of paclitaxel at the tumor site may result in slow release of the drug at the tumor site resulting in greater efficacy when compared to administration of the drug in its solubilized (Cremophor-containing) form.

An exemplary product according to the invention, referred to herein as ABI-007, is a novel Cremophor-free, protein stabilized nanoparticle formulation of paclitaxel. The major components are unmodified paclitaxel and human albumin (HA). HA is freely soluble in water. No premedication is required, as the risk of hypersensitivity is remote. A Phase I clinical study of ABI-007 in patients with solid tumors showed no hypersensitivity reactions following multiple IV administrations of this drug without any premedication.

Since the key ingredient of the trial product is paclitaxel, the mechanism of its action is identical to that of TAXOL and TAXOTERE™, another taxane used for similar conditions, both of which act as tubulin binding agents. Both promote microtubule assembly resulting in unusually stable tubulin complexes, which interfere with mitosis resulting in cell death.

Bristol Myers Squibb received approval of a New Drug Application for TAXOL for Injection Concentrate for the treatment of ovarian cancer in December, 1992 and for breast cancer in April, 1994. More recently, TAXOL was approved for use in AIDS-related Kaposi's Sarcoma and in non-small cell lung cancer. TAXOL has also demonstrated remarkable clinical activity in a number of human cancers including cancers of the lung, esophagus, head and neck region, bladder and lymphomas.

The mechanism of action of paclitaxel is well-known and is described in the literature. Paclitaxel is a novel anti-microtubule agent that promotes the assembly of microtubules from tubulin dimers, and stabilizes microtubules by preventing depolymerization. This stability results in the inhibition of the normal dynamic reorganization of the microtubule network that is essential for vital interphase and mitotic cellular function. In addition, paclitaxel induces abnormal arrays or "bundles" of microtubules throughout the cell cycle and multiple arrays of microtubules during mitosis.

Paclitaxel is insoluble in aqueous solutions. Therefore, a carrier vehicle must be used in order to administer paclitaxel intravenously. TAXOL utilizes a mixture of Cremophor EL® (polyoxyethylated castor oil) and approximately 50% dehydrated alcohol, USP as the vehicle for paclitaxel. Severe hypersensitivity and neutropenia, as well as other adverse effects, have been associated with the administration of TAXOL to both research animals and human patients.

In contrast to TAXOL, ABI-007 is a Cremophor-free formulation of paclitaxel nanoparticles stabilized with Human Albumin, USP as vehicle. This combination creates a colloid when reconstituted with saline, which is administered by intravenous infusion. By excluding toxic emulsifiers from ABI-007, it appears possible to administer higher doses of paclitaxel at more frequent intervals than currently possible with TAXOL, and without premedication.

Details of many aspects of the taxanes are discussed in the Physician Desk Reference, 1999, page 2609 for Taxotere and page 799 for Taxol and are incorporated by reference herein in their entirety.

While the invention composition and methods are described herein with reference to TAXOL, all pharmacologically active agents are contemplated for use in invention compositions and methods. For example, broad classes of compounds such as apoptosis inducing agents, antimitotic agents, microtubule or tubulin binding agents, taxanes, epothilones, COX-2 inhibitors, protease inhibitors, natural products of marine origin and their derivatives, marine polyketides such as discodermolide, eleutherobin, sarcodictyin A, and the like, in addition to compounds referenced in related patent applications, are contemplated for use in invention methods and compositions.

A nonlimiting list of epothilones, a new class of antitumor agents, useful for the invention compositions and methods have been referenced in an article by Nicolaou et al. (Angew. Chem. Int. Ed. 1998, 37, 2014–2045).

Invention compositions may be administered by intravenous (IV) infusion or intra-arterial administration over a desired period (e.g., bolus injection, 30 min, 1 hr, 2 hr, 3 hr, 6 hr, 24 hr, 48 hr, 72 hr or 96 hour infusions). Preferred period is no greater than about 3 hours.

For the treatment of brain tumors, e.g., glioblastomas, intra-arterial administration is preferred, especially via the carotid artery (distal to or proximal to the ophthalmic artery). Invention particles are capable of traversing the blood-brain barrier by passing through the leaky vessels supplying the tumor.

The administration or dosage cycle may be repeated in increments of 1 day, 1 week, 2 weeks, 3 weeks, 4 weeks, 5 weeks or may be repeated with a break in the cycle, for example 3 weeks on a weekly schedule with 1 week off.

Dosage range of invention compositions varies with the potency of the drug in question. For example drugs such as paclitaxel may be administered in a dose range of about 30–500 mg/m$^2$, docetaxel in the range of about 15–250 mg/m$^2$ and epothilones in the range of about 1–200 mg/m$^2$. These ranges are intended to be exemplary and not limiting.

A number of preclinical studies and Phase I open-label, dose-ranging clinical studies have been performed to demonstrate the safety, pharmacokinetics and the potential efficacy of ABI-007. The preclinical studies were a combination of in vitro cytotoxicity studies; efficacy studies in mice; acute toxicity studies in mice; acute toxicity studies in rats; studies of myelosuppression in rats; pharmacokinetics studies in rats and an acute toxicity study in dogs.

The in vitro cytotoxicity study in an in vitro tumor model using L1210 murine leukemia cells demonstrated that ABI-007 has equivalent efficacy to TAXOL.

Efficacy was greater for ABI-007 than TAXOL in female athymic Ncr-nu mice implanted with MX-1 mammary tumor fragments. One hundred percent (100%) of ABI-007-treated animals survived after 103 days compared to 20%–40% surviving in groups treated with equivalent doses of TAXOL.

In a series of three pharmacokinetic studies in rats, the pharmacokinetic profile of paclitaxel, formulated as ABI-007, and TAXOL were shown to be similar, but blood/tissue concentration ratios and rates of metabolism varied significantly. ABI-007 is more rapidly distributed out of the blood and is more slowly metabolized. Tissue levels of radio-labeled paclitaxel were higher in several tissues (prostate, spleen, pancreas, and to a lesser extent bone, kidney, lung, and muscle) following administration of ABI-007 when compared to TAXOL. Excretion of paclitaxel following ABI-007 and TAXOL administration was predominantly in the feces.

Toxicity studies have been conducted in mice, rats, and dogs. Single dose acute toxicity studies in mice showed an LD$_{50}$ dose approximately 59 times greater for ABI-007 than for TAXOL. In a multiple dose toxicity study in mice, the LD$_{50}$ dose was approximately 10 fold greater for ABI-007 than for TAXOL.

In a 14 day, acute toxicity study in rats, the animals tolerated ABI-007 at doses up to 120 mg/kg, whereas significant morbidity and mortality were reported at doses of 30 mg/kg of TAXOL. Cerebral cortical necrosis was seen in the TAXOL-treated animals. Testicular degeneration was observed in the ABI-007-treated animals.

A single-dose, acute toxicity study was conducted in dogs to determine if the differences observed in the pharmacokinetic profiles of paclitaxel, after doses of ABI-007 and TAXOL resulted in toxicities in a large animal species. The study was conducted using ABI-007, ABI-007 vehicle control, and Human Albumin, USP. TAXOL was not used because of the severe anaphylactic reaction known to be exhibited by dogs due to the Cremophor in the product. With the exception of testicular degeneration in the males (also seen in the rats), the study did not provide useful information. Animals in all groups (active drug and controls) exhibited significant symptoms, which were attributed to an immune reaction to human albumin.

Two further pilot studies were conducted to evaluate the degree of myelosuppression in rats treated with ABI-007 and TAXOL. The results showed that ABI-007 produces considerably less myelosuppression in rats than TAXOL at a dose of 5 mg/kg. The study of the effects of higher doses of ABI-007 (30, 90, 120, 200 mg/kg) showed a dose response relationship in both myelosuppression and decreased body weights with the effect peaking at day 3.

White blood cell counts were back to normal or were elevated by day 14 in surviving animals. Animals in the high dose study showed symptoms of dose-related toxicity.

In a Phase I, intravenous administration, open-label, dose-ranging trial of ABI-007 therapy in patients with advanced solid tumors conducted at M. D. Anderson Cancer Center, more than 80 courses of ABI-007 were administered intravenously over 30 minutes every 3 weeks to 19 patients. The total number of doses of ABI-007 administered was 83. The maximum dose administered was 375 mg/m$^2$, which was administered to six patients (between 25–85 minutes). The maximally tolerated dose was 300 mg/m$^2$, which was also administered to six patients (between 27–60 minutes). The following data for the Phase I study is preliminary, and is representative of all 19 patients; however, data is still outstanding on three patients, who are currently receiving study drug. The 375 mg/m$^2$ dose was associated with dose-limiting toxicities in three out of the six patients. At dose levels of 135 mg/m$^2$ and less than 200 mg/m$^2$, there were no adverse events of myelosuppression or peripheral neuropathy.

ABI-007 was well tolerated at doses up to 300 mg/m$^2$. Most adverse events were Grade 1 or 2 (93%), required no action (83%) and were resolved (78%). No deaths occurred during the study. Five patients had reductions in their study drug dosages, changes in their frequency, interruptions in dosing and/or discontinuation of study drug during the study. All five patients had these changes to their study drug regimen as the result of the development of unacceptable toxicities. Of these five patients, four reported sensory changes, three reported vision-related toxicities, two patients experienced asthenia and two patients experienced thrombocytopenia. All other patients receiving a dose from 135 mg/m$^2$ to 300 mg/m$^2$ showed no such evidence of thrombocytopenia.

There was a total of 13 (68.4%) patients that reported Absolute Neutrophil Count (ANC)<2000 cells/mm$^3$. Of the total 13 patients, 2 (15%) were at a dose level of 135 mg/m$^2$, 1 (8%) patient was at dose level 200 mg/m$^2$, 5 (38%) patients were at dose level 300 mg/m$^2$, and 5 (38%) patients with ANC<2000 cells/mm$^3$ were at the dose level of 375 mg/$\ell^2$.

Two (10.5%) patients experienced thrombocytopenia, both dosed at 375 mg/m$^2$. The first patient resolved when dosing level was reduced to 198.86 mg/m$^2$. The second patient resolved without any action taken; however, on the patient's next dosing cycle, study drug was administered at a slightly lower dose of 361.38 mg/m$^2$.

The most common (>3% of all 377 reported events) adverse events were asthenia (13.1%), nausea (8.8%), fever (6.8%), sensory changes (6.1%; sensory changes included: sensory loss, tingling, paresthesia, and peripheral neuropathy), arthralgia (5.7%), stomatitis (5.1%), myalgia and headache (both at 4.5%), diarrhea, rash, vomiting, and visual disturbances (all at 4.3%; visual disturbances included: vision abnormalities (2.0%), dry eyes (1.4%), and keratitis (0.9%)), and hypertonia (3.4%).

The adverse events reported by the majority of patients (% of total patients) were asthenia (84.21%), nausea (68.42%), sensory changes (63.16%), rash (57.89%), fever, myalgia, and stomatitis (all at 52.63%), headache (42.11%), diarrhea and vomiting (both at 36.84%), arthralgia (31.58%), and hypertonia (26.32%). Phase I Incidence of Adverse Events, categorized by the number (% of Total) of occurrences and number (% of Total) of patients for administration of ABI-007 is summarized in Table 5 (see Example 12).

Sensory changes and visual disturbances were the only toxicities that appeared to be dose-related. Sensory and vision-related toxicities were rated as Grade 2 and Grade 3, judged to be potentially study drug-related and required changes to the study drug-dosing regimen. Half of the cases reported at the time of the preliminary analysis remained unresolved. These were potentially dose-related toxicities in that 16 out of the 23 reported sensory toxicities and 6 out of the 17 vision-related toxicities occurred in patients receiving >300 mg/m$^2$.

Nineteen out of the 27 (70.4%) reporting Grade 3 toxicities were rated potentially study drug related. Only 4 (21%) out of the 19 remain unresolved: one fatigue and three cases of sensory changes. These four cases occurred in three different patients and action (study drug dose reduction) was required for only one case of sensory toxicity. Five cases of asthenia, which were rated as Grade 3, occurred in five separate patients. These toxicities were judged as potentially study drug-related in four cases, which required study drug dose regimen changes in two cases (both dosed at 375 mg/m$^2$). Grade 3 sensory changes occurred in four separate patients, all judged as potentially study drug-related and required dose reductions in three cases (patient dosed between 300–375 mg/m$^2$).

In addition, six patients developed potentially study drug related ocular problems, which required dose regimen changes in three cases. Ocular complaints included the following: decreased vision associated with burning sensation, foreign body sensation and photophobia. These patients were found to have superficial keratopathy as the underlying cause of their problems. They required aggressive lubrication and placement of collagen punctual plugs. These events were resolved after dose reduction and treatment of symptoms in two cases. This data is not inclusive of all resolutions. Two cases remained unresolved at the time of the preliminary analysis.

Two patients developed unacceptable toxicities, which warranted discontinuation from the study in the opinion of the Principal Investigator. The first patient received cycle one dosing of ABI-007 at 300 mg/m$^2$, and was reduced to 200 mg/m$^2$ due to subsequent development of Grade 1 arthralgia and Grade 3 sensory changes. This patient continued on the study for four additional cycles, with no acute toxicities. The second patient received one dosing cycle at 370.83 mg/m$^2$, with no acute toxicities; however, both patients later developed multiple toxicities and were discontinued from the study.

In conclusion, based on information available to date, ABI-007, a Cremophor-free nanoparticle formulation of paclitaxel, provides a new efficient method of treating patients with paclitaxel with lower toxicity to the patient, allowing treatment with higher therapeutic doses of the active drug substance, without the need for premedication.

Taxanes constitute a new antineoplastic class approved and administered since 1992 for the treatment of ovarian cancer and 1994 breast cancer. More recently, taxanes were approved for the use in Kaposi's sarcoma, in some human cancers including lung, esophagus, head and neck, bladder and lymphomas. As improved formulations of paclitaxel are developed, it is expected that additional indications will benefit from treatment with paclitaxel, e.g., glyblastomas.

Paclitaxel promotes the assembly of microtubules and stabilizes the microtubules by preventing depolymerization. This stability inhibits the normal dynamic reorganization of the microtubule that is essential for vital interphase and mitotic cellular function.

Paclitaxel is insoluble in aqueous solutions, therefore a carrier vehicle must be used, e.g., a mixture of polyoxyethylated castor oil (Cremophor EL) and dehydrated alcohol. Acute reactions such as hypotension, dispnea, bronchospasm, changes in heart rate, urticaria have been associated with the administration of this vehicle. For this reason it is required to perform a pre-medication with prednisone, cimeditine, clorfenamine and hydrocortisone. Severe leucopenia and neutropenia are less frequent in short administrations than in long infusions.

The new formulation of paclitaxel nanoparticles stabilized with human albumin (<200 nm), creating a colloid when reconstituted with saline, is easier to handle than the prior art paclitaxel-containing formulations, with an unchanged cytotoxicity and with an acute toxicity in the animal 60 times inferior to Taxol.

In research animals myelosuppression is inferior and the anaphylactic reactions are absent. The colloid shows chemical-physical characteristics suitable with the injection performed using very small catheters. Viscosity is low and is compatible with the plastic materials.

After endovenous administration the total tissue concentration of ABI-007 is higher than that observed with Taxol; in vivo, ABI-007 is slowly metabolized so the cytotoxic activity of ABI-007 is longer than the one reported with Taxol.

From preliminary observations it is possible to assess that taxanes are more active in the squamouscellular carcinoma because this type of tumours show a major presence of the growth factor receptor. The hypothesis is that the taxanes could interfere in the process mediated by the receptor.

Taxane activity per systemic treatment in the advanced head and neck carcinoma aren't numerous. The efficacy of paclitaxel per endovenous treatment as a single agent in the relapse is superior with respect to the standard chemotherapic combinations (cisplatin, 5 FU), however the improvement is not so relevant. Considering the recently developed taxanes, such as docetaxel, the objective responses (complete-partial response) in the relapses go from 30 to 42%.

Less than 30% of patients with advanced local tumours (state III/IV) can be subjected to surgery and/or radiotherapy.

Three cycles of Cisplatin-Fuorouracil treatment show a clinical complete response in the 30–50% of the patients with relevant toxicity. The improvement of patients' survival hasn't been observed with this neoadjuvant treatment, as a recovery of the loco-regional tumour or the presence of metastases have occurred. A high T takes to a local relapse and it's more difficult to obtain a clinical response or a complete pathological response.

The intent to improve the neoadjuvant chemotherapy in the oral and oro-hypopharynx carcinoma, is justified by assessing a final local therapy through surgery or radiotherapy in order to reach a good life-style or to protect the organ.

An intra-arterial chemotherapy with cytostatics was conducted in the past and recently resumed after cisplatin introduction; moreover the technique and the new material for catheterism permitted to improve the procedure reducing the risks. The response registered (clinical-radiological complete and partial) goes from 47 to 94% in patients with advanced disease or relapse.

At Istituto Nazionale per lo Studio e la Cura dei Tumouri did Milano (INT) is going to close a phase I study with ABI-007 intra-arterial administration in solid tumour especially loco-regional type with the enrolment of about 100 patients.

Twenty-three patients with squamous-cellular head and neck carcinoma, stage IV, not treated (10), with relapse after surgery+RT+chemotherapy (5), surgery+radiotherapy (3), radiotherapy+chemotherapy (1), surgery+chemotherapy (2), radiotherapy (1), surgery (1). ABI-007 was administered intra-arterial every 4 weeks for 3 cycles. The maximum dose was of 270 mg/m$^2$.

All 23 patients were evaluable for toxicity : 86.36% alopecia (I, II), 77.27% simile-flu syndrome (I, II), 68.18% midollar (I-II, 1 Pt grade 4), 45.45% neurological (I-II), 50% gastro-intestinal (I-II), 27.27% cutaneous (I-II) and 22.72% ocular (I-II). In 80 cases evaluated, one serious adverse event occurred. One patient with head and neck carcinoma with concomitant cirrhosis died after esophageal varices rupture. In this case, the dose was 300 mg/m$^2$ and caused a grade IV haematological toxicity.

The efficacy was assessed in 20 patients valuable for T: CR (pathological) 2 (10%), PR 12 (60%), MR (15%), SD (15%), PRO 2 (10%).

The complications using catheterization of cerebral vessels evaluated on 23 patients for 60 procedures are 5%. Three patients suffered from hemi paresis (1 case) a temporary cerebral ischaemia; these complications are spontaneously recovered.

The quality of life in patients subjected to intra-arterial therapy was remarkable with a local and systemic toxicity acceptable, especially with ABI-007 (230 mg/m$^2$ dose). This dose will be administered each 4 weeks (±3 days) for the Phase II study.

The invention will now be described in greater detail by reference to the following non-limiting examples.

EXAMPLE 1

Reconstitution and Use

Invention compositions are dosage forms containing 30 mg, 100 mg or 300 mg of paclitaxel in a vial.

When reconstituted with 0.9% Sodium Chloride Injection, USP, ABI-007 forms a colloidal suspension of paclitaxel stabilized with Human Albumin, USP. The formulation contains no other added excipients. The sterility of the product is assured by an aseptic manufacturing process and sterile filtration.

The two major components of ABI-007 are paclitaxel and Human Albumin, USP. Since human albumin is soluble in Sodium Chloride Injection, USP, ABI-007 can be reconstituted to the desired concentration of paclitaxel, which is limited only by the solubility limits for human albumin.

Administration of ABI-007 to the patient can be accomplished by intravenous infusion at a dosage directed in the clinical protocol. At any given dose of paclitaxel in mg/m$^2$, the total mg of paclitaxel to be administered should be calculated by the physician, using the height/weight conversion chart for body surface area of the patient.

Reconstitution and use of invention formulation can be accomplished as follows:

Calculate the patient's body surface area by using the height/weight chart;

Calculate the total mg required by the patient;

Calculate the total number of vials required by the patient;

Under a biological safety cabinet, using sterile technique, reconstitute each vial by injecting a suitable quantity of 0.9% Sodium Chloride Injection, USP to achieve the desired administration concentration (0.2–40 mg/ml) with a preferred range of 2–10 mg/ml;

After reconstitution, agitate by gentle mixing before use (avoid generation of foam);

Allow 20 minutes for complete suspension and dissolution;

Gently agitate again to ensure complete resuspension prior to administration;

The reconstituted sample should be milky and homogeneous without visible particulates. If particulates are visible, the vial should be mildly agitated again to ensure complete re-suspension, prior to use;

Inject the reconstituted ABI-007 into an empty sterile, plastic type IV bag, using an injection site. Inject perpendicularly into the center of the injection site, to avoid dislodging plastic material into the IV bag. Use a new 60 cc syringe after every two injections into the I.V. bag;

Remove the injection site; and

Administer the reconstituted ABI-007 solution by IV infusion over a desired period (e.g., bolus injection, 30 min, 1 hr, 2 hr, 3 hr, 6 hr, 24 hr, 48 hr, 72 hr or 96 hour infusions). Preferred administration period is no greater than about 3 hours. Do not use in-line filters, as they are not necessary.

EXAMPLE 2

Stability of Invention Compositions

Invention compositions and dosage forms in polymeric or glass containers were diluted with sterile normal saline to concentrations of 0.5, 1, 5, 10, and 15 mg/ml. and stored at room temperature and under refrigerated conditions. The compositions were found to be homogeneous and stable for at least 24 hours to three days under these conditions. Particle size measurements performed at several time points indicated no change in size distribution. No precipitation was seen under these conditions.

In addition, the diluted compositions were stable in the presence of different polymeric materials such as teflon, silastic, polyethylene, tygon, and other standard infusion tubing materials. The compositions were stable under frozen, refrigerated as well as room temperature conditions.

Stability studies of the non-diluted invention compositons show stability under refrigerated and room temperature conditions for over 1 year. Freezing, refrigeration or room temperature storage does not adversely affect the product.

EXAMPLE 3

Dissolution and Release of Drug from Invention Compositions

Once the compositions are diluted with saline or dextrose or other aqueous medium, the drug becomes available or is released in solution. Different dissolution media may be utilized for example, media containing surfactants such as tweens, proteins such as serum albumin, etc. to measure release and availability of the drug. Dissolution and release testing are performed by techniques well described in the art.

It is found that a majority of the drug is released from invention compositions of paclitaxel within 24 hours.

EXAMPLE 4

Dosage forms

Dosage forms of invention compositions are prepared in unit vessels of glass, metallic, organic, inorganic or polymeric origin or combinations thereof with suitable closures that are glass, metallic, organic, inorganic or polymeric in origin or combinations thereof. Depending on the potency of invention composition drugs, the unit vessels may contain between 1 mg to 1000 mg of active drug. Suitable dosage forms include but are not limited to 5 mg, 10 mg, 20 mg, 30 mg, 50 mg, 80 mg, 100 mg, 150 mg, 200 mg, 250 mg, 300 mg, 350 mg, 400 mg, 450 mg, 500 mg, 600 mg, 800 mg, 1000 mg. These dosage forms are stable when stored frozen, refrigerated or at room temperature and for select periods at elevated temperatures.

EXAMPLE 5

Anti-tumor Efficacy of ABI-007 in Animals

The pharmacology of paclitaxel is well understood and is described in the literature. Paclitaxel is a novel anti-microtubule agent that promotes the assembly of microtubules from tubulin dimers and stabilizes microtubules by preventing depolymerization. The stability results in the inhibition of the normal dynamic reorganization of the microtubule network that is essential for the vital interphase and mitotic cellular function. In addition, paclitaxel induces abnormal arrays or "bundles" of microtubules throughout the cell cycle and multiple arrays of microtubules during mitosis. It has recently been reported that paclitaxel facilitates apoptosis in cells containing the Bcl-2 gene. It is postulated that paclitaxel phosphorylates the Bcl-2 gene and induces programmed cell death. Several tumors are known to be Bcl-2 positive (prostate tumors).

A pilot study has been conducted to determine the efficacy of the ABI-007 formulation of paclitaxel. Female athymic NCr-nu mice were implanted with MX-1 human mammary tumor fragments and treated with daily (five days) injections of ABI-007, ABI-007 vehicle and TAXOL. The efficacy of ABI-007 was demonstrated with 100% survival of the animals in the high dose group (45 mg/kg/day) of both formulations of ABI-007. In contrast, no animals survived after receiving vehicle, and only 40% of animals survived on the highest dose of TAXOL (30 mg/kg/day).

The antitumor activity of ABI-007 was also demonstrated in an in vitro study. Murine leukemia cells (L1210) were cultured in suspension and dilutions of ABI-007 or TAXOL (0.01 to 0.5 μg/mL) were added to the cell cultures in Falcon 96-well plates. Cells were counted after 48 hours.

Both ABI-007 and TAXOL exhibited antitumor activity in L1210 murine leukemia cells. The $IC_{50}$ for ABI-007 and TAXOL were 0.014 μg/mL and 0.010 μg/mL respectively. The slightly lower $IC_{50}$ for TAXOL is probably caused by the toxic effect of the Cremophor/ethanol vehicle.

EXAMPLE 6

Pharmacokinetics and Product Metabolism in Animals

Two studies were performed to compare the pharmacokinetics and tissue distribution of $^3$H-paclitaxel formulated in ABI-007 and TAXOL. Male rats received intravenous injections of either 10 mg/kg or 5 mg/kg of $^3$H-TAXOL. A third group of rats received intravenous injections of 5 mg/kg $^3$H-ABI-007.

Levels of both total radioactivity and paclitaxel declined bi-phasically in blood of rats following 5 mg/kg IV bolus doses of either $^3$H-TAXOL or $^3$H-ABI-007. However, the levels of both total and paclitaxel in blood were significantly lower for $^3$H-ABI-007 at a similar dose as $^3$H-TAXOL dose.

$^3$H-ABI-007 and $^3$H-TAXOL exhibited a similar pattern of paclitaxel metabolism into highly polar metabolite(s) as measured by blood HPLC profile; however, metabolism appeared significantly slower for $^3$H-ABI-007 with 44.2% of blood radioactivity remaining as paclitaxel at 24 hours post-dose versus 22.4% for $^3$H-TAXOL. The excretion of radioactivity occurred only minimally in the urine and predominantly in the feces for $^3$H-ABI-007, which is similar to the reported excretion patterns for $^3$H-TAXOL.

The blood kinetics for total radioactivity and paclitaxel following IV administration of $^3$H-ABI-007 or $^3$H-TAXOL at 5 mg/kg are presented in Table 3.

TABLE 3

Kinetics for Total Radioactivity and Paclitaxel Following Intravenous Dosing

| Treatment | $AUC_{0-24}$ (μg eq.hr/ mL) | Extrapolated $C_0$ (μg eq/mL) | Observed $C_{max}$ (μg eq/mL) | Observed $T_{max}$ (hr) | $t_{1/2}\beta$ (hr) |
|---|---|---|---|---|---|
| Total Radioactivity | | | | | |
| $^3$H-ABI-007 | 6.1 | 7.6 | 4.2 | 0.03 | 19.0 |
| $^3$H-TAXOL | 10.2 | 19.7 | 13.5 | 0.03 | 19.7 |
| Paclitaxel | | | | | |
| $^3$H-ABI-007 | 3.7 | 7.0 | 4.0 | 0.03 | 11.4 |
| $^3$H-TAXOL | 5.4 | 17.1 | 11.8 | 0.03 | 7.2 |

Tissue radioactivity levels are higher following $^3$H-ABI-007 administration than $^3$H-TAXOL administration for 9 of 14 tissues. $^3$H-ABI-007 was present in significantly greater quantities than $^3$H-TAXOL in prostate, spleen, and pancreas and to a lesser extent in bone, kidney, lung, heart and muscle. The tissue/blood concentration ratios were higher in all tissues for the $^3$H-ABI-007 dosed animals as a result of the lower blood levels. This supports the rapid distribution of $^3$H-ABI-007 from the blood to the tissues suggested by the blood kinetic data. $^3$H-paclitaxel formulated in ABI-007 showed a similar pharmacokinetic profile to $^3$H-paclitaxel formulated in TAXOL, but tissue/blood concentration ratios and metabolism rates differ significantly. A significantly lower level of total radioactivity was detected for ABI-007-treated animals than for TAXOL-treated animals in the 2-minute post administration blood sample, indicating that the $^3$H-ABI-007 is more rapidly distributed out of the blood.

In a third study, four additional groups of rats were treated with a single bolus dose of 9.1 mg/kg, 26.4 mg/kg, 116.7 mg/kg, and 148.1 mg/kg of paclitaxel in $^3$H-ABI-007. Blood was collected from the tail vein and the $AUC_{0-24}$ was calculated. At 24 hours, blood samples were collected, extracted, and the extract analyzed by HPLC to determine the level of parent compound in the blood. Higher bolus doses of $^3$H-TAXOL were not tested because of the death of 5 of 14 animals at 10 mg/kg in a previous study.

The blood kinetics for total radioactivity and paclitaxel following IV administration of $^3$H-ABI-007 are presented in Table 4.

TABLE 4

Kinetics for Total Radioactivity and Paclitaxel Following IV Dosing

| Group/Dose (mg/kg) | $AUC_{0-24}$ ($\mu$g eq.hr/mL) | Extrapolated $C_0$ ($\mu$g eq/mL) | Observed $C_{max}$ ($\mu$g eq/mL) | Observed $T_{max}$ (hr) | $t_{1/2}\beta$ (hr) |
|---|---|---|---|---|---|
| A/9.1 | 11.5 | 10.2 | 7.19 | 0.03 | 22.3 |
| B/26.4 | 43.5 | 44.8 | 29.5 | 0.03 | 16.0 |
| C/116.7 | 248.9 | 644.6 | 283.3 | 0.03 | 8.48 |
| D/148.1 | 355.3 | 1009.8 | 414.2 | 0.03 | 9.34 |

As the dose of paclitaxel was increased, the area under the curve was proportionally increased. The level of parent compound after 24 hours was increased by a factor of 8.5 (0.04 ppm–0.34 ppm), going from the 9 mg/kg dose to the 148 mg/kg dose.

$^3$H-ABI-007 was well-tolerated as a single IV bolus at all four doses tested. The plot of the AUC for total radioactivity versus IV dose administered shows a linear, but disproportionate response with a slope greater than one. This response was also observed when comparing 5 and 10 mg/kg doses of $^3$H-TAXOL tested in previous studies. HPLC analysis of 24-hour post-dose blood samples showed a significant percentage (7–19%) of blood activity as unchanged paclitaxel, indicating that paclitaxel in ABI-007 is slowly metabolized in vivo and that total exposure to paclitaxel is significant for ABI-007-treated animals. Paclitaxel is not a new drug substance. Preclinical studies of ABI-007 have therefore been limited to specific studies which evaluate the toxicity of the new formulation and the potential use of higher doses of paclitaxel in humans than is currently approved.

EXAMPLE 7

Toxicology in Mice

A pilot study was conducted to compare the $LD_{50}$ of ABI-007, TAXOL and their carrier vehicles following a single bolus intravenous administration into mice. The results indicated that paclitaxel administered in ABI-007 is less toxic than TAXOL or the TAXOL vehicle administered alone. The $LD_{50}$ and $L_{10}$ for ABI-007 were 447.4 and 371.5 mg/kg of paclitaxel, 7.53 and 5.13 mg/kg of paclitaxel in TAXOL, and 1325 and 794 mg/kg of the TAXOL vehicle (corresponds to a dose of 15.06 and 9.06 mg/kg TAXOL), respectively. In this study, the $LD_{50}$ for ABI-007 was 59 times greater than TAXOL and 29 times greater than the TAXOL vehicle alone. Most deaths in the TAXOL and TAXOL vehicle treated groups occurred on day 0 which suggests the toxicity of TAXOL is due to an acute reaction to the vehicle. Such acute reactions are unlikely to occur in human patients treated with ABI-007 because of the difference in vehicles.

A pilot study was conducted to compare the $LD_{50}$ of ABI-007 and TAXOL following daily (five days) intravenous administrations into mice. The results indicated that ABI-007 is less toxic than TAXOL. The $LD_{50}$ of ABI-007 was 76.2 mg/kg of paclitaxel, compared to 8.07 mg/kg of paclitaxel in TAXOL. In this study, the $LD_{50}$ for ABI-007 was 9.4 times higher than for TAXOL. All deaths (11) for TAXOL-treated animals occurred on days 0–4 after start of treatment while deaths for ABI-007-treated animals (5) occurred on days 6 or 9 after the start of treatment. The results of this study suggest that the ABI-007 is less toxic than TAXOL when administered in multiple doses at daily intervals. Human patients will initially receive ABI-007 infusion over a period of approximately 30 minutes with 3-week intervals between treatments, rather than a 1 day interval as in the animal studies. Toxicity from treatment with ABI-007 is considerably less than treatment with TAXOL.

EXAMPLE 8

Toxicology in Rats

A further study was conducted to determine the toxicity of ABI-007 following a single IV administration at approximately 1 mL/minute with a total volume of 5 mL/kg to 6 male and 6 female rats at each dose of 5, 9, 30, 90 and 120 mg/kg.

One half of the animals from each group were euthanized and necropsied on day 8. The remaining animals were necropsied on day 31. The results of the ABI-007 treated animals were compared to the results of normal saline and vehicle control groups, as well as to the results of animals treated with 5, 9 and 30 mg/kg TAXOL.

Thirteen rats died in the study. Twelve of the animals treated with 30 mg/kg TAXOL® and one treated with ABI-007 died on day 4. In comparison, all but one animal treated with ABI-007 at doses up to and including 120 mg/kg survived. One animal treated with 90 mg/kg ABI-007 had an unexplained death.

Animals were observed for overt manifestations of toxicity immediately following dosing, 1 hour and 4 hours post-administration and once daily for 7 or 30 days. All animals in each group appeared normal immediately post-administration. At 1 and 4 hours post-administration, rats in the TAXOL-treated groups were observed to have piloerection and staggering gaits.

This reaction was possibly due to the high alcohol content of the TAXOL vehicle. Animals treated with ABI-007 at doses up to and including 30 mg/kg were normal throughout the 7 day and 30 day observation periods. A few incidents of piloerection were reported in animals treated with 90 and 120 mg/kg of ABI-007.

Male rats in the 120 mg/kg ABI-007 treated group had reduced body weights at day 8 when compared to the control animals. The animals did recover some of the lost weight by the end of the study.

Hematology and serum chemistries were generally unremarkable in this study. The most notable findings were a tendency towards marginally high sodium concentrations and correspondingly low potassium concentrations in the animals treated with higher doses of ABI-007. Despite statistical significance when compared to controls, this high concentration of sodium was still within normal parameters. Animals treated with 120 mg/kg ABI-007 were reported to have a high BUN concentration on day 8, but values returned to normal by day 31.

At necropsy, significant lesions were observed in the male reproductive organs of animals dosed with 9, 30, 90 and 120 mg/kg ABI-007. These changes involved diffuse degeneration and necrosis of the testis. These changes were most prevalent in animals that received higher doses of ABI-007. Female rats did not demonstrate toxic effects from ABI-007 doses up to and including 120 mg/kg. ABI-007 was considerably less toxic than TAXOL. No TAXOL-treated animals survived at doses higher than 9 mg/kg.

With the exception of an incidental death at 90 mg/kg ABI-007, all animals survived doses to 120 mg/kg. Human patients should also experience less toxic effects with ABI-007 treatment than with TAXOL.

EXAMPLE 9

Myelosuppression in Rats

Myelosuppression and other hemopoietic effects have been reported as adverse events after treatment with TAXOL. A pilot study was designed to compare the effects of ABI-007 with TAXOL in rats after a single intravenous injection. The effects of both the ABI-007 and TAXOL carrier vehicles were also tested. Both ABI-007 and TAXOL were tested at a single dose of 5 mg/kg paclitaxel while the carrier vehicles were tested individually at the respective concentrations used to suspend 5 mg/kg of paclitaxel. Therefore, 766 mg/kg of TAXOL vehicle and 50 mg/kg of ABI-007 vehicle were administered for these treatments. Four male rats were treated per test group by infusion over 3 hours. Changes in body weight and white blood cell counts were monitored for 14 days post treatment to evaluate the hemopoietic effects.

ABI-007 produced significantly less ($P<0.05$) myelosuppression than TAXOL as determined by white cell counts at days 1 and 7 and a highly significant ($P<0.01$) reduction in white cell counts at 10. The recovery period from the white blood cell suppression after a 5 mg/kg dose of paclitaxel was only about 7 days for ABI-007 but was about 14 days for TAXOL. ABI-007 also showed significantly less decreases in weight at days 1 and 10 than TAXOL. The TAXOL vehicle (Cremophor/ethanol) had a very strong neutropenic effect. The TAXOL vehicle decreased WBCs for days 1 and 3 ($P<0.01$) when compared to the ABI-007 vehicle and also significantly decreased WBCs on day 1 when compared to ABI-007 ($P<0.05$). Significant decreases in body weights ($P<0.05$) were also observed for the TAXOL vehicle when compared to both ABI-007 and its vehicle.

This suggests that the TAXOL vehicle may be the major cause of myelosuppression from TAXOL. However, the ABI-007 vehicle (human albumin) showed no significant myelosuppression in this study. Therefore, neutropenia from treatment in human patients with ABI-007 should be considerably less than treatment than with TAXOL.

EXAMPLE 10

Canine Toxicology

The animals in all three treatment groups exhibited a common syndrome of gastrointestinal symptoms, edema, vasculitis, and organ and tissue abnormalities. These toxic effects indicate that the animals were reacting to human albumin, a constituent of the formulation common to all three groups. That ABI-007-treated animals had more severe and numerous clinical symptoms suggests that the cytotoxic effects of paclitaxel in the ABI-007 exacerbated the effects of the human albumin.

The effects seen in ABI-007-treated animals other than the common syndrome, are consistent with changes seen in other paclitaxel studies. However, the toxicity of ABI-007 at 175 mg/m$^2$ was not established in this study.

EXAMPLE 11

Phase I Clinical Study of Intravenous ABI-007 in Solid Tumors

In a Phase I, open-label, dose-ranging trial of ABI-007 therapy in patients with advanced solid tumors conducted at M. D. Anderson Cancer Center, more than 80 courses of ABI-007 were administered intravenously (IV) over 30 minutes, every 3 weeks to 19 patients. The total number of doses of ABI-007 administered was 83. The maximum dose administered was 375 mg/m$^2$, which was administered to six patients (between 25–85 minutes). The maximally tolerated dose was determined to be 300 mg/m$^2$, which was also administered to six patients (between 27–60 minutes).

The following data for the Phase I study is preliminary, and is representative of all 19 evaluable patients entered into the study; however, data is still outstanding on three patients, who are currently receiving study drug. The Phase I study has been closed for enrollment and the maximum tolerated dose (MTD) for ABI-007 has been established to be 300 mg/m$^2$.

Patient Demographics

Of the 19 enrolled patients, 3 (15.8%) were male and 16 (84.2%) were female. Median age was 51 years (range: 34–83 years). The majority of patients were white 18 (94.7%). One patient was Hispanic (5.3%).

Patient Diagnoses and Condition

The primary diagnoses for the 19 patients enrolled were as follows: Six (31.6%) patients had melanoma, 12 (63.2%) had breast cancer and 1 (5.3%) had a primary diagnosis of unknown origin. Histology showed 11 (57.9%) patients diagnosed with invasive ductal carcinoma; 6 (31.6%) patients had malignant melanoma; 1 (5.3%) patient diagnosed with invasive lobular carcinoma, and 1 (5.3%) patient with Paget's disease of the nipple. At baseline all 19 patients reported having a Zubrod performance status score of 2 or less. Eleven (57.9%) patients reported having a Zubrod score of 1. Four (21.1%) patients reported a score of 0, and 4 (21.1%) patients reported a score of 2.

Baseline Physical Examination and Labs

The majority of patients had an abnormal physical examination (p.e.) at baseline. Sixteen (84.2%) patients had abnormal physical exams, 2 (10.5%) patients had a normal p.e., and baseline p.e. data was missing on 1 (5.3%) patient. The median weight at baseline was 70.7 kg (range: 46.9–100.7). The median systolic blood pressure was 118 (range: 96–180) and diastolic was 74 (range: 50–96). Median laboratory values at baseline versus median laboratory values during all dosing cycles of the study are displayed below:

| Lab | Baseline Median Lab Values | Median Values Throughout the Study |
|---|---|---|
| HGB | 11.6 (range: 8–14.3) | 11.2 (range: 7.4–14.6) |
| PLT | 243.5 (range: 154–509) | 253 (range: 25–585) |
| WBC | 5.9 (range: 3.2–11.9) | 4 (range: 0.4–32) |
| NEUTS (%) | 69 (range: 59–84) | 63.9 (range: 3–94) |

Prior Therapy

All 19 patients had received prior therapy. Nineteen (100%) patients had prior chemotherapy; 6 (31.6%) patients had prior hormonotherapy; 7 (36.8%) patients had prior immunotherapy; 17 (89.5%) patients had prior radiotherapy; and 17 (89.5%) patients had prior surgery.

Relevant Prior Chemotherapy

All 19 patients had received prior chemotherapy. Twelve (63.2%) had previously received doxorubicin; 8 (42.1%) had received Taxol, and 2 (10.5%) had received Herceptin. Patients had received many other commonly used drugs.

Dose Escalation

Four dose levels were utilized in this study. The starting dose level of ABI-007 was 135 mg/m$^2$. Four patients were treated at this dose. The dose was escalated by 50% to 200 mg/m$^2$, at which 3 patients were treated. The dose was further escalated by 50% to 300 mg/m$^2$ at which 6 patients were treated. The final escalation in dose was by 25% to 375 mg/m$^2$ at which 6 patients were treated. It was eventually determined that 300 mg/m$^2$ was the maximum tolerated dose (MTD). At dose levels of 135 mg/m$^2$ and less than 200 mg/m$^2$, there were no adverse events of myelosuppression or peripheral neuropathy.

EXAMPLE 12

Intravenous ABI-007: Safety and Toxicity

ABI-007 was well tolerated at doses up to 300 mg/m$^2$, which were delivered over a period of 27–60 minutes. Most adverse events were Grade 1 or 2 (93%), required no action (83%) and were resolved (78%). No deaths occurred during the study. Five patients had reductions in their study drug dosages, changes in their frequency, interruptions in dosing and/or discontinuation of study drug during the study. All five patients had these changes to their study drug regimen as the result of the development of unacceptable toxicities. Of these five patients, four reported sensory changes, three reported vision-related toxicities, two experienced asthenia, and two patients experienced thrombocytopenia. All other patients receiving a dose from 135 mg/m$^2$ to 300 mg/m$^2$ showed no such evidence of thrombocytopenia.

The most common ($\geq$3% of all 377 reported events) adverse events were asthenia (13.1%), nausea (8.8%), fever (6.8%), sensory changes (6.1%; sensory changes included: sensory loss, tingling, paresthesia, and peripheral neuropathy), arthralgia (5.7%), stomatitis (5.1%), myalgia and headache (both at 4.5%), diarrhea, rash, vomiting and visual disturbances (all at 4.3%; visual disturbances included: vision abnormalities (2.0%), dry eyes (1.4%), and keratitis (0.9%)), and hypertonia (3.4%).

The adverse events reported by the majority of patients (given as % of patients) were asthenia (84.21%), nausea (68.42%), sensory changes (63.16%), rash (57.89%), fever, myalgia, and stomatitis (all at 52.63%), headache (42.11%), diarrhea and vomiting (both at 36.84%), arthralgia (31.58%) and hypertonia (26.32%). Sensory changes and visual disturbances were the only toxicities which appeared to be dose-related. Sixteen out of the 23 reported sensory toxicities and 6 out of the 17 vision-related toxicities occurred in patients receiving $\geq$300 mg/m$^2$.

Grade 3 Toxicities

There were 27 occurrences of Grade 3 reported toxicities, including: fatigue and sensory changes, both at 5 (19.2%), stomatitis 3 (11.5%), diarrhea and keratitis, both at 2 (7.7%), bone pain, constipation, cough, dyspnea, hypoxia, infection, nausea, pleural effusion, skin reaction, and vomiting all were reported as single occurrences (3.8%). (% of total is reflective of the number of occurrences out of the total 27 Grade 3 reported toxicities.)

Nineteen out of the 27 (70.4%) reported Grade 3 toxicities were rated potentially study drug related. Only 4 (21%) out of the 19 remain unresolved; one fatigue and three cases of sensory changes. These four cases occurred in three different patients and action (study drug dose reduction) was required for only one case of sensory toxicity.

Hematologic Toxicities

There was a total of 13 (68.4%) patients that reported an Absolute Neutrophil Count (ANC)<2000 cells/mm$^3$. Of the total 13 patients, 2 (15%) were at a dose level of 135 mg/m$^2$, 1 (8%) patient was at dose level 200 mg/m$^2$, 5 (38%) patients were at dose level 300 mg/m$^2$, and 5 (38%) patients with ANC<2000 cells/mm$^3$ were at the dose level of 375 mg/m$^2$. Two patients, at dosing level 375 mg/m$^2$, resolved without any action taken; however, on their following cycle both patients under went a dose reduction due to thrombocytopenia and one case of Grade 3 skin reaction, 198.86 mg/m$^2$ and 361.3 mg/m$^2$, respectively.

Two (10.5%) patients experienced thrombocytopenia, both dosed at 375 mg/m$^2$. The first patient resolved when dosing level was reduced to 198.86 mg/m$^2$. The second patient resolved without any action taken; however, on the patient's next dosing cycle, study drug was administered at a slightly lower dose of 361.38 mg/m$^2$. All other patients receiving a dose from 135 mg/m$^2$ to 300 mg/m$^2$ showed no such evidence of thrombocytopenia.

Sensory Toxicities

Sensory changes (including sensory loss, tingling, paresthesia, and peripheral neuropathy) were reported by 12 (63.16%) out of 19 patients. There were a total of 23 reported occurrences of sensory toxicities. Eight (34.8%) occurrences of sensory toxicity were reported as Grade 1 (including two patients with pre-existing condition at baseline). A total of 10 (43.5%) occurrences of sensory toxicity were rated as Grade 2 and 5 (21.7%) reported cases were rated as Grade 3. Two out of the 23 (8.7%) occurrences were pre-existing sensory toxicities experienced by two patients prior to study drug administration. These two patients went on to receive study drug and there were no reports of any sensory toxicities while receiving ABI-007. Five out of the 23 (21.7%) occurrences took place at dosing levels of 200 mg/m$^2$ to <300 mg/m$^2$. Sixteen out of the 23 (70%) occurrences were at dosing levels >300 mg/m$^2$. Ten (43.5%) occurrences out of the 23 reported sensory toxicities occurred at dosing levels >370 mg/m$^2$. Action was taken on only four out of the total 23 sensory reported toxicities. Two patients discontinued study drug for the remainder of the cycle, one patient was at dose level 375.28 mg/m$^2$ and the second patient was at 370.83 mg/m$^2$; however, they both resumed their following cycle at a dose reduced study drug level, 198.86 mg/m$^2$ and 300 mg/m$^2$, respectively. The third patient reported a Grade 3 sensory toxicity while at a dosing level of 301.07 mg/m$^2$. Patient continued on the next cycle at a dose reduced level of 198.93 mg/m$^2$. The fourth patient (dosing level 301.50 mg/m$^2$) experienced a Grade 2 sensory toxicity. Study dose level was reduced to 200 mg/m² for the following cycle.

Considering that 2 of the 12 patients included amongst those reporting sensory changes had pre-existing sensory toxicities prior to receiving the study drug and that these patients did not report any further sensory changes while on the study, it may be concluded that sensory changes occurred in 10 (52.6%) out of 19 patients while they were on the study drug. Grade 3 sensory toxicities occurred in 4 (21%) of 19 patients.

Ocular or Vision Toxicities

A total of 17 occurrences of visual disturbances, including decreased vision associated with burning sensation, foreign body sensation and photophobia were reported by 10 (52.6%) patients while receiving ABI-007. In the opinion of the Investigator, 10 (63%) of the 17 visual toxicities were possibly study drug related.

Six (35%) of the reported cases were classified as definitely study drug related. One (6%) occurrence rated as a Grade 2 was classified as not study drug related. Of the 16 occurrences that were possibly or definitely study drug related, 9 (56%) were rated Grade 1, 5 (31%) were Grade 2, and 2 (12.5%) were rated as Grade 3. Ten (58.8%) occurrences required no action to be taken. The single occurrence that was classified as not study drug related required treatment for symptoms only. Six (35%) occurrences required action. These six occurrences were among three patients. The first patient experienced three separate visual disturbances: blurred vision (Grade 2), keratitis (Grade 3) and another occurrence of blurred vision (Grade 1), all at dose level 375.28 mg/m². Patient's study drug regimen was interrupted; however, the patient continued on the following cycle at a dose reduced level of 198.86 mg/m². The second patient requiring action, experienced one occurrence of Grade 2 abnormal vision and a Grade 3 keratitis. Dosing regimen of 370.83 mg/m² was interrupted; however, patient resumed dosing at a reduced level of 300 mg/m². The third patient had a Grade 2 occurrence of keratitis while receiving ABI-007 at a dosing level of 301.50 mg/m². Action taken was a dose reduction on the following cycle to 200 mg/m². These symptoms were resolved by aggressive lubrication and placement of collagen punctal plugs.

The incidence of adverse events for the above-described Phase 1 study are summarized in Table 5.

TABLE 5

Summary table of Toxicities

| ADVERSE EVENT | Number (% of Total) of Occurrences | Number (% of Total) of Patients |
|---|---|---|
| Alopecia | 10(2.8%) | 10(52.6%) |
| Amblyopia | 3(0.8%) | 2(10.5%) |
| Anorexia | 9(2.5%) | 8(42.1%) |
| Anxiety | 2(0.6%) | 2(10.5%) |
| Arthralgia | 20(5.7%) | 6(31.6%) |
| Asthenia | 46(13.0%) | 15(78.9%) |
| Chills | 6(1.7%) | 1(5.3%) |
| Constipation | 10(2.8%) | 9(47.4%) |
| Convulsions | 1(0.3%) | 1(5.3%) |
| Cough, Increased | 2(0.6%) | 1(5.3%) |
| Cramps Leg | 1(0.3%) | 1(5.3%) |
| Depression | 3(0.8%) | 3(15.8%) |
| Diarrhea | 15(4.2%) | 7(36.8%) |
| Dyspepsia | 3(0.8%) | 2(10.5%) |
| Dyspnea | 3(0.8%) | 3(15.8%) |
| Dysuria | 1(0.3%) | 1(5.3%) |
| Ear Disorder | 2(0.6%) | 2(10.5%) |
| Edema | 2(0.6%) | 2(10.5%) |
| Effusion Pleural | 1(0.3%) | 1(5.3%) |

TABLE 5-continued

Summary table of Toxicities

| ADVERSE EVENT | Number (% of Total) of Occurrences | Number (% of Total) of Patients |
|---|---|---|
| Emotional Lability | 1(0.3%) | 1(5.3%) |
| Fever | 24(6.8%) | 10(52.6%) |
| Flu Syndrome | 7(2.0%) | 3(15.8%) |
| Headache | 16(4.5%) | 8(42.1%) |
| Hem Vaginal | 1(0.3%) | 1(5.3%) |
| Hypertonia | 12(3.4%) | 5(26.3%) |
| Hypokalem | 1(0.3%) | 1(5.3%) |
| Hypoxia | 1(0.3%) | 1(5.3%) |
| Infection | 5(1.4%) | 5(26.3%) |
| Infect Urin Tract | 1(0.3%) | 1(5.3%) |
| Infect Viral | 1(0.3%) | 1(5.3%) |
| Insomnia | 9(2.5%) | 6(31.6%) |
| LDH, Increased | 1(0.3%) | 1(5.3%) |
| Leukopenia | 1(0.3%) | 1(5.3%) |
| Liver Func Abnormality | 1(0.3%) | 1(5.3%) |
| Myalgia | 16(4.5%) | 10(52.6%) |
| Nail Disorder | 1(0.3%) | 1(5.3%) |
| Nausea | 31(8.8%) | 13(68.4%) |
| Pain | 1(0.3%) | 1(5.3%) |
| Pain, Abdominal | 2(0.6%) | 2(10.5%) |
| Pain Bone | 4(1.1%) | 3(15.8%) |
| Pain Chest | 1(0.3%) | 1(5.3%) |
| Pharyngitis | 2(0.6%) | 2(10.5%) |
| Polyuria | 2(0.6%) | 2(10.5%) |
| Rash | 15(4.2%) | 11(57.9%) |
| Rhinitis | 3(0.8%) | 2(10.5%) |
| Sensory Changes | 23(6.0%) | 12(63.2%) |
| Speech Disorder | 1(0.3%) | 1(5.3%) |
| Stomatitis | 18(5.1%) | 10(52.6%) |
| Syncope | 1(0.3%) | 1(5.3%) |
| Thirst | 3(0.8%) | 3(15.8%) |
| Vasodilation | 1(0.3%) | 1(5.3%) |
| Visual Disturbance | 17(4.5%) | 10(52.6%) |
| Vomiting | 15(4.2%) | 7(36.8%) |

EXAMPLE 13

Comparison of Toxicities of ABI-007, TAXOL and TAXOTERE

Sensory toxicities (including sensory loss, tingling, paresthesia, and peripheral neuropathy) with ABI-007 occurred in 52.6% of patients while they were on the study drug. In comparison, peripheral neuropathy occurred in 70% of patients receiving TAXOL and neurosensory toxicities occurred in 56.8% of patients receiving TAXOTERE.

No hypersensitivity reactions were observed with ABI-007, whereas hypersensitivity was experienced in 36% of patients receiving TAXOL, and 17.6% of patients receiving TAXOTERE.

These findings suggest that at equivalent or higher doses of ABI-007 in this limited population, a much lower incidence of toxicity is observed in the ABI-007 group.

The MTD for ABI-007 was established at 300 mg/m². Preliminary, unaudited data from the Phase I trial of ABI-007 (given at 135–375 mg/m²/30 min) indicate a lower incidence of adverse events than seen with the published information on TAXOL (given at 175 mg/m²/3 hr) and TAXOTERE (given at 100 mg/m²/1 hr).

ABI-007 indicates 68% of patients reporting neutropenia at <2000 cells/m³, compared to TAXOL (90%) and TAXOTERE indicating 98.5%. ABI-007 indicates 32% of patients (4 out of 6 patients at dose level 375 mg/m²) experiencing neutropenia at <500 cells/m³ compared to TAXOL (28%) and TAXOTERE (85.9%).

EXAMPLE 14

Clinical Pharmacokinetics of ABI-007

In Phase I of this trial, 19 patients with solid tumor/breast cancer were assigned to four cohorts of at least 3 patients each. The starting ABI-007 dose at 135 mg/m² was administered to the first cohort via intravenous infusion at 3-week intervals. After a minimum of 3 patients in the first cohort had been treated with the starting dose infused over 180 minutes, the infusion duration was decreased to 30 minutes. The ABI-007 doses for the three remaining cohorts were 200, 300, and 375 mg/m², respectively, with each ABI-007 dose infused over a duration of approximately 30 minutes.

Sixteen of the 19 patients entered into the study contributed analyzable pharmacokinetic profiles. Following the termination of ABI-007 intravenous infusion in individual patients, the decline from maximum plasma concentration was biphasic. Pharmacokinetic analysis of individual patient profiles yielded pertinent pharmacokinetic parameters, which are summarized in Table 6.

TABLE 6

Summary of Non-Compartment Pharmacokinetic Parameters Mean (% Coefficient of Variation) Values by Single Dose and Infusion

| Dose (mg/m²) | Infusion Duration (min) | N | $C_{max}$ (ng/mL) | $AUC_{inf}$ (ng.h/mL) | Half-Life (h) | CL (L/h/m²) | $V_z$ (L/m²) |
|---|---|---|---|---|---|---|---|
| 135 | 180 | 3 | 1392 (30) | 5654 (42) | 12.9 (60) | 27.4 (45) | 418 (32) |
| 135 | 30 | 1 | 6100 | 6427 | 14.6 | 21.1 | 442 |
| 200 | 30 | 3 | 7757 (35) | 9613 (20) | 13.4 (67) | 21.4 (21) | 384 (64) |
| 300 | 27–30 | 5 | 13520 (7) | 17610 (21) | 14.6 (14) | 17.7 (22) | 370 (23) |
| 375 | 30–45 | 4 | 19350 (15) | 35805 (40) | 13.2 (12) | 11.9 (42) | 236 (54) |

N Number of patients
$C_{max}$ Maximum or peak concentration
$AUC_{inf}$ Area under the whole blood/plasma concentration-time curve from time zero to time infinity
CL Total body clearance
$V_z$ Volume of distribution The paclitaxel $AUC_{inf}$ value increased exponentially versus ABI-007 dose. This dose-dependent pharmacokinetic behavior was reflected by decreasing CL values as the ABI-007 dose was raised from 135 mg/m² to 375 mg/m². Similar findings have been reported Taxol.

Furthermore, based on a visual inspection the ABI-007 pharmacokinetic parameters obtained in the present study versus published pharmacokinetic parameters for Taxol, both products produced similar paclitaxel $AUC_{inf}$, half-life, and plasma clearance values at similar doses. However, ABI-007 could be infused intravenously over a shorter duration, i.e., 30 to 45 minutes compared to the intravenous infusion of Taxol, which normally takes 3 to 24 hours.

Protocol DM97-123 is an open non-randomized Phase I/II trial of ABI-007 in patients with solid tumor/breast cancer. In Phase I of this protocol, 19 patients were entered and were assigned to four cohorts of at least 3 patients each. The starting ABI-007 dose at 135 mg/m² was administered to the first cohort via intravenous infusion at 3-week intervals. After a minimum of 3 patients in the first cohort had been treated with the starting dose infused over 180 minutes, the infusion duration was decreased to 30 minutes. The ABI-007 doses for the three remaining cohorts were 200, 300, and 375 mg/m², respectively, with each ABI-007 dose infused over a duration of approximately 30 minutes.

This preliminary clinical pharmacokinetic report summarizes the results of the pharmacokinetic analysis of the patients who contributed analyzable plasma drug concentration profiles.

Each cohort had a minimum of 3 patients. Each patient received ABI-007 via intravenous infusion at 3-week intervals. The ABI-007 infusion duration varied from 27 minutes to 180 minutes depending on the targeted ABI-007 dose.

| Targeted ABI-007 Dose (mg/m²) | Patient Number | Infusion Duration (min) |
|---|---|---|
| 135 | 1, 2, 3 | 180 |
|  | 4 | 30 |
| 200 | 5, 6, 7 | 30 |
| 300 | 8, 9, 11, 12, 13 | 27–30 |
| 375 | 15, 16, 17, 19 | 30–45 |

Whole blood/plasma samples were collected from each patient at baseline and at 0.25, 0.5, 1, 1.5, 2, 4, 6, 8, 12, 14, 24 and 48 hours from the start of the first intravenous infusion of ABI-007. The whole blood/plasma samples were frozen and shipped on dry ice to Alta Analytical Laboratories, El Dorado Hills, Calif. for assay of paclitaxel concentrations. A highly specific and sensitive LC/MS/MS assay was used in the analysis of whole blood/plasma samples. The limit of quantification of the assay was 5 ng/mL.

Plasma samples were obtained from all four patients assigned to receive the starting ABI-007 dose at 135 mg/m² and from the first patient in the second cohort assigned to receive ABI-007 dose at 200 mg/m². Whole blood samples were collected from the remaining patients.

Nineteen patients (16 females and 3 males) were enrolled. There were 18 Caucasians (95%) and 1 Hispanic (5%). The median age was 51 years (range: 34–83 years). Sixteen of the 19 enrolled patients contributed analyzable plasma drug concentration profiles. Of these 16 patients, 4 were assigned to receive ABI-007 at 135 mg/m², 3 were assigned to receive ABI-007 at 200 mg/m², 5 were assigned to receive ABI-007 at 300 mg/m², and 4 were assigned to receive ABI-007 at 375 mg/m².

Pharmacokinetic parameters were determined from each patient's whole blood/plasma paclitaxel concentration profile. The non-compartmental routine in WinNonlin was used in the analysis. The peak or maximum paclitaxel concentration ($C_{max}$) and the corresponding peak time ($t_{max}$) were observed values. The elimination constant ($\lambda_z$) was obtained by log-linear regression analysis of the terminal phase of the whole blood/plasma concentration versus time profile. The elimination half-life ($T_{1/2}$) was determined by taking the ratio of natural log of 2 and $\lambda_z$. The area under the curve from time zero to time infinity ($AUC_{inf}$) was obtained by summation of $AUC_{last}$ (area under the curve from time zero to last measurable concentration, calculated by the linear trapezoidal rule) and $AUC_{ext}$ (extrapolated area, estimated by taking the ratio between the last measurable concentration and $\lambda_z$). The dose-area relationship (i.e., total ABI-007 dose divided by $AUC_{inf}$) was used to determine total body clearance (CL). The volume of distribution ($V_z$) was determined by taking the ratio between CL and $\lambda_z$.

Descriptive statistics (mean, median, standard deviation, coefficient of variation, maximum and minimum) were computed for pertinent pharmacokinetic parameters by ABI- 007 dose. No inferential statistics were performed due to the small sample size per cohort. However, linear regression analysis of $AUC_{inf}$ versus dose was performed to gain an appreciation of pharmacokinetic linearity, if evident, for the dose range evaluated in this trial.

Sixteen of the 19 patients entered into the study contributed analyzable pharmacokinetic profiles. The individual patient plasma paclitaxel concentration versus time profile, plotted in both Cartesian and semi-log coordinates. Figures showed the mean semi-log plasma paclitaxel concentration versus time plots for the four targeted ABI-007 doses. Both the individual patient plots and the mean profiles showed that plasma paclitaxel concentration climbed from the origin to maximum concentration (occurring at the termination of ABI-007 intravenous infusion). It is of interest to note the decline from maximum plasma paclitaxel concentration was biphasic.

Non-compartmental analysis of individual profiles yielded pertinent pharmacokinetic parameters for each patient. A listing of the individual pharmacokinetic parameter values (including $C_{max}$, $T_{max}$, $T_{1/2}$, $AUC_{inf}$, CL and $V_z$) was also provided by patient number. A summary of pharmacokinetic parameters by targeted ABI-007 dose is presented in the Table above.

The mean $AUC_{inf}$ values increased more than proportionally versus ABI-007 dose. This non-linear pharmacokinetic behavior was also reflected by a decreasing CL term as the ABI-007 dose was raised.

The results of linear regression analysis of $AUC_{inf}$ values versus dose showed that only 67% of the change in $AUC_{inf}$ value could be explained by increases in ABI-007 dose. Similar dose dependent pharmacokinetic findings have been reported for Taxol (please see Taxol package insert).

Furthermore, based on a visual inspection the ABI-007 pharmacokinetic parameters obtained in the present study versus published pharmacokinetic parameters for Taxol, both products produced similar paclitaxel $AUC_{inf}$, half-life, and plasma clearance values at similar doses. However, the present study showed that ABI-007 could be infused intravenously over a shorter duration, i.e., 30 to 45 minutes compared intravenous infusion of Taxol, which normally takes 3 to 24 hours.

ABI-007, a Cremophor-free formulation of paclitaxel, offers the advantage of short intravenous infusion duration (e.g., 30 to 40 minutes) while achieving similar $AUC_{inf}$ values as TAXOL.

EXAMPLE 15

Summary of Data

All of the animal studies comparing ABI-007 to TAXOL have shown lower toxicity with ABI-007 and that it is the Cremophor EL vehicle, in part, that causes some of the toxicity associated with the TAXOL formulation of paclitaxel. These studies also indicate that paclitaxel in the ABI-007 formulation has the same efficacy in treating carcinomas as paclitaxel in the TAXOL formulation but with the advantage of lower toxicity as demonstrated by higher $LD_{50}$ values for both single and multiple dose administrations and lower neutropenia. Another advantage appears to be that higher doses can be safely administered. A Phase I study in 19 patients with solid tumors established a maximum tolerated dose of 300 mg/m². There were no cases of hypersensitivity. Side effects at all doses up to 375 mg/m² included asthenia, nausea, fever, myalgia, headache, vomiting, diarrhea, arthralgia, rash, stomatitis, sensory changes, visual disturbances, constipation, and flu-like symptoms. Dose-related adverse events were sensory changes and vision disturbances, which occurred at doses $\geq 200$ mg/m². The specific ocular complaints were described as decreased vision associated with burning sensation, foreign body sensation and photophobia. These symptoms were resolved with dose reduction and treatment. Also, the precautions and risks reported for TAXOL must be considered in the ABI-007 clinical trials. Adverse reactions that may occur are those that are attributed to the components of ABI-007 (paclitaxel and human albumin). These adverse reactions include neutropenia; thrombocytopenia; anemia; peripheral neuropathy; mucositis; myalgia/arthralgia; diarrhea; alopecia; elevation in bilirubin, alkaline phosphates and AST (SGOT); injection site reactions; and allergic reactions characterized primarily by fever and chills, rash, nausea, vomiting, tachycardia, hypotension, and the like. These reactions are described in the package inserts for TAXOL, TAXOTERE and for HUMAN ALBUMIN GRIFOLS®.

Patients who experience severe hypersensitivity reactions to ABI-007 should not be re-challenged with the drug. There are no studies on pregnant or nursing women. These patients will be excluded from receiving this therapy. Females of childbearing age should take appropriate precautions to prevent pregnancy. In addition, one of the preclinical animal studies indicated degenerative lesions in the seminal vesicles and prostates of male rats treated with higher doses of paclitaxel in ABI-007. Therefore, male patients should be made aware of the possible risks to reproductive function.

As with all new pharmaceuticals in Phase I and II trials, there are possible, unknown risks. Therefore, both the treating physicians and patients must be vigilant to note and report any unusual occurrences or conditions. However, based on all the data presently available, ABI-007 is an effective pharmaceutical for treating patients with higher doses of paclitaxel than used previously and with less severe toxic effects.

EXAMPLE 16

Phase I Clinical Study of Intra-arterial ABI-007 for Loco-regional Solid Tumors

In a Phase I, intra-arterial administration, open-label, dose-ranging trial of ABI-007 therapy in patients with advanced loco-regional solid tumors conducted at Insituto Nazionale Tumori, more than 200 courses of ABI-007 were administered intra-arterially over 30 minutes every 4 weeks to over 90 patients. The phase I study, open-label, in patients with loco-regional solid tumors is still ongoing. One hundred patients are planned.

The following data is preliminary and is representative of 74 patients (31 female and 43 male all of white race). Demographic data are reported in the attached tables.

The primary diagnosis of the 74 patients enrolled were as follows: 28 had hepatic-carcinoma (7 primary tumor, 21 secondary tumor) the remaining 46 had tumor in different districts: anal canal (12), bladder (6), head (16), neck (5), lung (2), pancreas (2), uterus (1), vulvae (1) e supernal (1).

Mean and median values concerning weight, height and age were reported and divided for type of tumors. Patients with liver carcinoma were treated with single doses between 150–450 mg for a maximum of three cycles. Patients with solid tumors received dose between 150–510 mg for a maximum of 4 cycles.

EXAMPLE 17

Phase I Clinical Study of Intra-arterial ABI-007: Toxicity

Twenty-four patients with hepatic carcinoma and 45 patients with solid tumors showed 98 and 301 adverse events, respectively. Most events have been observed in the following: cutaneous (alopecia), systemic (asthenia and fever), gastro-intestinal (nausea, vomiting and stomatitis) and haematopoietic (anemia and leucopenia).

One patient with head carcinoma died during the study. The death occurred 6 days after the first cycle (dose 450 mg) due to heart failure; the patient was hospitalized and was diagnosed with hepatic failure and severe midollar deficiency. The Investigator judged the event possibly related to the study drug, but the current hepatic cirrhosis could have increased the toxicity. In patients with hepatic carcinoma, the intensity of the events was judged mild in 57.1% of the cases and moderate in the 42.8%; the 58.1% of the events do not require assistance and the 82.6% of the events recovered without sequelae for the patient. Then the investigator judged related to the study drug the 77.5% of the events (probable 35.7% and possible 41.8%). Concerning the solid tumors, the event intensity was mild in the 71.0%, moderate in the 26.5% and severe in the 2.3% of the cases; the 78% of the events do not require assistance and all the events recovered without sequelae in 67.4% of the cases. The drug correlation was of the 77.7% (probable in the 39.5% and possible in the 38.2 of the cases).

The events related to the study drug, have been judged in terms of toxicity according to WHO criteria. In patients with hepatic-carcinoma (primary tumor) the following intensity has been observed: grade 1 in 76.9% of the cases (23.1% epigastralgia, 15.4% leucopenia e 15.4% alopecia), grade 2 in the 15.4% of the cases (alopecia). One patient showed a grade 3 stomatitis (7.7%).

In patients with hepatic-carcinoma (secondary tumor) the events with grade 1 are the 82.5% of the cases (15.8% leucopenia, 12.3% nausea, 12.3% anemia, and 10.5% asthenia), with grade 2 the 17.5% of the cases (12.3% alopecia). No patient reported superior grade toxicity. In case of solid tumor, the toxicity has been valuated for each type of tumor. In solid tumors the most common toxicity events (grade 1) were alopecia, asthenia, leucopenia, anemia and paresthesias. Alopecia, asthenia, leucopenia and stomatitis were the common events observed and judged of grade 2 toxicity. In patients with anal canal tumors were registered two cases of leucopenia classified of grade 3 and 4.

Laboratory values do not indicate changes clinically significant; the only relevant changes have already been documented as adverse events and if considered related to the study drug, have been valuated as toxicity events according to WHO toxicity grade.

EXAMPLE 18

Phase I Clinical Study of Intra-arterial ABI-007: Efficacy

Seventy-two patients have been analysed in terms of efficacy data instead of 74 analysed for the toxicity data (Intention-to-treat), as the above-mentioned patient (with head carcinoma), died after the first cycle without performing any efficacy evaluation. The second patient (with vulvae carcinoma) was excluded from the analysis as lost to follow-up after the first cycle.

The response is defined according to WHO criteria, partial in 3 cases (11%), stable disease in 13 (46%) and progression in 12 (43%) patients with hepatic carcinoma (28).

Patients with head and neck carcinoma (20) showed a complete response in 2 cases (9.5%), partial in 14 cases (66.7%), stable in 2 cases (9.5%) and progression in 2 cases (9.5%).

Patients with anal canal carcinoma (12) showed a complete response in 1 case (8.3%), partial in 4 cases (33.4%), stable in 6 cases (50%) and progression in 1 case (8.3%).

Patients with bladder carcinoma (6) showed partial response in 5 cases (83.3%) and stable disease in 1 case (16.7%).

The remaining 6 patients (with lung, uterus, pancreatic and suprarenal carcinoma) showed partial response in 1 case (uterus), stable in 2 cases (lung, pancreas) and progression in the last 3 cases (lung, pancreas and suprarenal).

EXAMPLE 19

Invention Compositions Comprising Devices for Delivery in Conjunction with Pharmacological Agents Invention compositions, e.g., those containing drugs such as taxanes, are utilized in conjunction with devices for delivery in order to treat subjects in need of the medication or pharmacological agents. Devices contemplated for use with invention compositions include any type of tubing including polymeric tubings that may be utilized to administer the invention compositions or in general to administer drugs such as the taxanes or other antiproliferative drugs. Tubings of interest for use in the invention include catheters of any type, intravenous lines, arterial lines, intra-thecal lines, intracranial lines, catheters or tubing that may be guided by suitable means to any location within the subject, e.g., to the site of a stenotic blood vessel such as coronary artery or other artery or vein. Such tubings may also have the capability to carry balloons or stents that are useful for treatment of local narrowing, stenosis, restenosis, plaques including atherosclerotic plaques, thrombotic lesions, sites of hyperplasia, aneurysms or weakness in blood vessels.

Devices such as stents are also contemplated for use in combination with invention compositions. Stents may be fabricated from organic or inorganic materials, polymeric materials or metals. Invention compositions contemplate the combination of the invention pharmacological agents and devices mentioned herein.

Combination devices such as those comprising tubings along with balloons, stents, devices for local injection (e.g., into the lumen, into the vessel wall, into the intima of the blood vessel, into the endothelial or sub-endothelial layer, into the smooth muscle layer of blood vessels) etc. are also contemplated in combination with invention compositions of pharmacological agents.

Invention compositions of pharmacological agents or in general drugs such as the taxanes or other antiproliferative drugs and any drug or drugs contemplated by the invention may be delivered by the devices described above either by flowing through the device, being impregnated or embedded or stored within or with the device, or being able to be released or delivered at a local site of interest by the device or delivered by the device to be systemically available in the subject (e.g., intravenous administration).

While the invention has been described in detail with reference to certain preferred embodiments thereof, it will be understood that modifications and variations are within the spirit and scope of that which is described and claimed.

That which is claimed is:

1. A method for the delivery of substantially water insoluble pharmacologically active agents to a subject, said method comprising administering to said subject an effective amount of composition prepared by subjecting a mixture comprising:

an organic phase containing said pharmacologically active agents dispersed therein, and aqueous medium containing biocompatible polymer, wherein said mixture optionally contains substantially no surfactants, to high shear conditions in a high pressure homogenized at a pressure in the range of about 100 up to 100,000 psi.

2. A method according to claim 1 wherein said composition further comprises one or more of albumin, a polyalkylene glycol, or an oil.

3. A method according to claim 2 wherein said oil is an oil-soluble vitamin.

4. A method according to claim 3 wherein said vitamin is vitamin A, vitamin D, vitamin E or vitamin K.

5. A method according to claim 1 wherein said pharmacologically active agent is selected from the group of an anti-neoplastic, an anesthetic and a hormone.

6. A method according to claim 5 wherein said anti-neoplastic is a taxane.

7. A method according to claim 1 wherein said pharmacologically active agent is non-crystalline.

8. A method according to claim 5 wherein said anesthetic is propofol.

9. A method according to claim 5 wherein said hormone is a thyroid hormone.

10. A method for eliminating cancer cells with a cremophor free oncolytic comprising particles of an antineoplastic coated with protein, wherein said protein coating has free protein associated therewith, wherein a portion of said antineoplastic is contained within said protein coating and a portion of said antineoplastic is associated with said free protein, and wherein the average diameter of said particles is no greater than about 1 micron.

11. A method according to claim 10 wherein the average diameter of said particles is less than 200 nm.

12. A method according to claim 11 wherein said cremophor free onolytic is sterile filtered.

13. A method according to claim 10 wherein said particles are amorphous, crystalline, or a mixture thereof.

14. A method according to claim 13 wherein said particles are substantially amorphous.

15. A method according to claim 10 wherein said antineoplastic is paclitaxel and said protein is albumin.

16. A method for reducing liver sequestration of pharmaceutical agents, said method comprising administering an effective amount of said pharmaceutical agent as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

17. A method according to claim 16 wherein said pharmacologically active agent is paclitaxel and said protein is albumin.

18. A method according to claim 16 wherein said pharmaceutical agent is selected from the group consisting of an anti-neoplastic, an anesthetic and a hormone.

19. A method according to claim 18 wherein said anti-neoplastic is a taxane.

20. A method according to claim 18 wherein said anesthetic is propofol.

21. A method according to claim 18 wherein said hormone is a thyroid hormone.

22. A method for the administration of paclitaxel to a patient in need thereof employing a dosing solution containing >1 mg/ml of paclitaxel, said method comprising administering said paclitaxel as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

23. A method for the administration of paclitaxel to a patient in need thereof employing a total infusion volume for each effective dose of <300 ml of paclitaxel-containing medium, said method comprising administering said paclitaxel as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

24. A method for the rapid administration of paclitaxel to a patient in need thereof, said method comprising administering said paclitaxel as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

25. A method of administering a pharmacologically active agent which must be administered in multiple doses, said method comprising administering the pharmacologically active agent, as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron, over a reduced cycle time.

26. A method according to claim 25 wherein said pharmacologically active agent is selected from the group consisting of an anti-neoplastic, an anesthetic and a hormone.

27. A method according to claim 26 wherein said anti-neoplastic is a taxane.

28. A method according to claim 26 wherein said anesthetic is propofol.

29. A method according to claim 26 wherein said hormone is a thyroid hormone.

30. A method of reducing the myelosuppressive effects of a pharmacologically active agent administered to a patient in need thereof, said method comprising administering the pharmacologically active agent, as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron, over a reduced cycle time.

31. A method of reducing the neurotoxic effects of a pharmacologically active agent administered to a patient in need thereof, said method comprising administering the pharmacologically active agent, as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron, over a reduced cycle time.

32. A method of administering pharmacologically active agent(s) to a patient having a disease capable of treatment by the pharmacologically active agent(s), said method comprising administering to the patient the pharmacologically active agent(s), as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

33. The method of claim 32, wherein the disease is a proliferative disease and the pharmacologically active agent(s) comprises an anti-neoplastic agent.

34. The method of claim 32, wherein the disease is a cancer treatable by systemic administration of pharmacologically active agent(s), the administration is intravenous, and the pharmacologically active agent(s) comprises an anti-neoplastic agent.

35. The method of claim 32, wherein the disease is a cancer treatable by systemic administration of pharmacologically active agent(s), the administration is intraarterial, and the pharmacologically active agent(s) comprises an anti-neoplastic agent.

36. The method of claim 32, wherein the administration of the composition is done without administration corticosteroid premedication.

37. The method of claim 36, wherein the administration of the composition is done in combination with administration of biochemotherapy agent(s).

38. The method of claim 32, wherein the administration of the composition is done without administration of cytokines.

39. A method according to claim 32 wherein said pharmacologically active agent is non-crystalline.

40. A method of delivering pharmacologically active agent(s) to a localized area of a patient for sustained release of the pharmacologically active agent over an extended period of time, said method comprising administering to the patient the pharmacologically active agent(s), as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron, wherein the composition has been dispersed within a matrix of suitable biocompatible material prior to administration to the patient.

41. A method according to claim 40 wherein said pharmacologically active agent is selected from the group consisting of an anti-neoplastic, an anesthetic and a hormone.

42. A method according to claim 41 wherein said anti-neoplastic is a taxane.

43. A method according to claim 41 wherein said anti-neoplastic is propofol.

44. A method according to claim 41 wherein said hormone is a thyroid hormone.

45. A method of orally administering pharmacologically active agent(s) to a patient in need thereof, said method comprising orally administering the pharmacologically active agent(s), as part of a drug delivery system comprising particles of a solid or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron, in combination with intestinal cell efflux inhibitor(s).

46. A method according to claim 45 wherein said pharmacologically active agent is selected from the group consisting of an anti-neoplastic and a hormone.

47. A method according to claim 45 wherein said anti-neoplastic is a taxane.

48. A method according to claim 45 wherein said hormone is a thyroid hormone.

49. A method of administering a combination of pharmacologically active agent(s) to a patient in need thereof, said method comprising administering to the patient 25–75% of the generally accepted effective dosage level of each of the pharmacologically active agent(s), as part of a drug delivery system comprising particles of a solid, or liquid, substantially water insoluble pharmacologically active agent, coated with protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

50. A method according to claim 49 wherein said pharmacologically active agent is selected from the group consisting of an anti-neoplastic, an anesthetic and a hormone.

51. A method according to claim 50 wherein said anti-neoplastic is a taxane.

52. A method according to claim 50 wherein said anesthetic is propofol.

53. A method according to claim 50 wherein said hormone is a thyroid hormone.

* * * * *

UNITED STATES PATENT AND TRADEMARK OFFICE
CERTIFICATE OF CORRECTION

PATENT NO.     : 6,537,579 B1
DATED          : March 25, 2003
INVENTOR(S)    : Neil P. Desai and Patrick Soon-Shiong It is certified that error appears in the above-identified patent and that said Letters Patent is hereby corrected as shown below:

Column 31,
Line 16, after "group" insert the word -- consisting --
Line 39, change "onolytic" to -- oncolytic --

Column 33,
Line 66, after "administration" insert the word -- of --

Signed and Sealed this

Nineteenth Day of August, 2003

JAMES E. ROGAN
*Director of the United States Patent and Trademark Office*